US009783520B2

(12) United States Patent
Foley et al.

(10) Patent No.: US 9,783,520 B2
(45) Date of Patent: Oct. 10, 2017

(54) MACROCYCLIC COMPOUNDS, POLYMERS, AND METHODS FOR MAKING SAME

(71) Applicant: P2 Science, Inc., Woodbridge, CT (US)

(72) Inventors: Patrick Foley, New Haven, CT (US); Yonghua Yang, New Haven, CT (US)

(73) Assignee: P2 SCIENCE, INC., Woodbridge, CT (US)

( * ) Notice: Subject to any disclaimer, the term of this patent is extended or adjusted under 35 U.S.C. 154(b) by 0 days.

(21) Appl. No.: 15/311,269

(22) PCT Filed: May 15, 2015

(86) PCT No.: PCT/US2015/031151
§ 371 (c)(1),
(2) Date: Nov. 15, 2016

(87) PCT Pub. No.: WO2015/175978
PCT Pub. Date: Nov. 19, 2015

(65) Prior Publication Data
US 2017/0088536 A1    Mar. 30, 2017

Related U.S. Application Data

(60) Provisional application No. 62/024,776, filed on Jul. 15, 2014, provisional application No. 61/994,545, filed on May 16, 2014.

(51) Int. Cl.
C07D 321/00    (2006.01)
(52) U.S. Cl.
CPC ............................. *C07D 321/00* (2013.01)

(58) Field of Classification Search
None
See application file for complete search history.

(56) References Cited

U.S. PATENT DOCUMENTS

| 2,020,298 A | 11/1935 | Carothers et al. |
| 3,980,697 A | 9/1976 | El-Chahawi et al. |
| 4,218,379 A | 8/1980 | Harris et al. |
| 4,366,270 A | 12/1982 | Ruter |
| 5,264,547 A | 11/1993 | Yamaguchi et al. |

FOREIGN PATENT DOCUMENTS

| EP | 0841333 A1 | 5/1998 |
| GB | 1266091 | 3/1972 |

OTHER PUBLICATIONS

Cahn et al. "Specification of Molecular Chirality", *Angew. Chem. Inter. Edit.* 1966, vol. 5, No. 4, pp. 385-415.
Cahn and Ingold, "Specification of Configuration about Quadricovalent Asymmetric Atoms" *J. Chem. Soc.* 1951, pp. 612-622.
Cahn et al., "The Specification of Asymmetric Configuration in Organic Chemistry", *Experientia*, 1956, vol. 12, pp. 81-94.
Cahn "An Introduction to the Sequence Rule. A system for the specification of absolute configuration", *Journal of Chemical Education*, 1964, vol. 41, No. 3, pp. 116-125.
Williams "The Synthesis of Macrocyclic Musks" *Synthesis* 1999, No. 10, pp. 1707-1723.
Yu and Sun "Macrocyclic Drugs and Synthetic Methodologies toward Macrocycles", *Molecules* 2013, vol. 18, pp. 6230-6268.

*Primary Examiner* — Timothy R Rozof
(74) *Attorney, Agent, or Firm* — Hoxie & Associates LLC

(57) ABSTRACT

The application relates to macrocyclic compounds and related polymers, as well as to processes for synthesizing them, e.g., using olefins as starting material.

20 Claims, 4 Drawing Sheets

MACROCYCLIC COMPOUNDS, POLYMERS, AND METHODS FOR MAKING SAME

RELATED APPLICATIONS

This application is a U.S. National Phase application, filed under 35 U.S.C. §371(c), of International Application No. PCT/US2015/031151, filed May 15, 2015, which claims priority to, and the benefit of, U.S. provisional application Nos. 61/994,545, filed May 16, 2014, and 62/024,776, filed Jul. 15, 2014. The entireties of each of which are incorporated herein by reference for all purposes.

BACKGROUND

Macrocyclic compounds have found use as biologically active compounds with commercial applications ranging from antibiotics to olfactory active compounds, specifically musks. Many approaches to the synthesis of macrocyclic compounds, and specifically macrolactones, have been developed, including coupled polymerization and depolymerization of polyesters, and ring expansion of cyclic ketones (see, e.g., U.S. Pat. No. 2,020,298, DE 2,026,056, and EP 0,841,333). Reviews of macrolactonization approaches can be found in, e.g., *Synthesis* 1999, 10, 1707-1723 and *Molecules* 2013, 18, 6230-6268.

New macrolactonization approaches that allow for the use of different starting materials and the incorporation of new functional groups are desired.

SUMMARY

In one aspect, the application features a compound according to Formula I or Formula II:

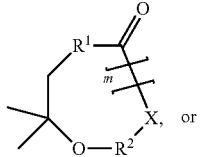
Formula I

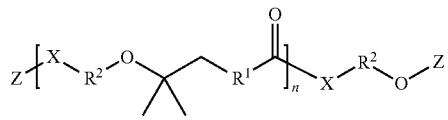
Formula II or a salt thereof, wherein,
$R^1$ is a bond, optionally substituted $C_1$-$C_{12}$ alkyl, optionally substituted $C_2$-$C_{12}$ alkenyl, or optionally substituted $C_2$-$C_{12}$ alkynyl;
$R^2$ is optionally substituted $C_1$-$C_{12}$ alkyl, optionally substituted $C_2$-$C_{12}$ alkenyl, or optionally substituted $C_2$-$C_{12}$ alkynyl;
X is O or $NR^x$;
$R^x$ is hydrogen or optionally substituted $C_1$-$C_{12}$ alkyl;
Z is hydrogen or

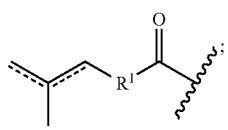

one of the ==== is a double bond and the other ==== is a single bond;
m is an integer between 1 and 10; and
n is an integer between 1 and 100,000.

In another aspect, the application features a method of producing a compound of Formula I and/or Formula II, a salt thereof, or a combination thereof. The method includes reacting a compound of Formula III or Formula IV:

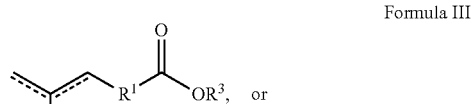
Formula III

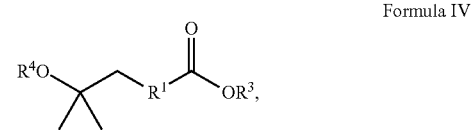
Formula IV with a compound of Formula V:

Formula V to obtain a reaction mixture comprising a compound of Formula I or Formula II, a salt thereof, or a combination thereof:

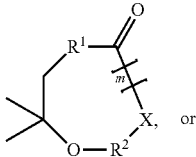
Formula I

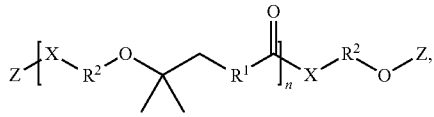
Formula II wherein,
$R^1$ is a bond, optionally substituted $C_1$-$C_{12}$ alkyl, optionally substituted $C_2$-$C_{12}$ alkenyl, or optionally substituted $C_2$-$C_{12}$ alkynyl;
$R^2$ is optionally substituted $C_1$-$C_{12}$ alkyl, optionally substituted $C_2$-$C_{12}$ alkenyl, or optionally substituted $C_2$-$C_{12}$ alkynyl;
$R^3$ is hydrogen, optionally substituted $C_1$-$C_{12}$ alkyl, optionally substituted $C_2$-$C_{12}$ alkenyl, or optionally substituted $C_2$-$C_{12}$ alkynyl;
$R^4$ is hydrogen, optionally substituted $C_1$-$C_{12}$ alkyl, optionally substituted $C_2$-$C_{12}$ alkenyl, or optionally substituted $C_2$-$C_{12}$ alkynyl;

X is O or NR$^x$;
R$^x$ is hydrogen or optionally substituted C$_1$-C$_{12}$ alkyl;
Z is hydrogen or

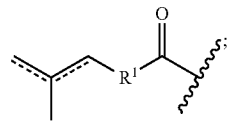

one of the ==== is a double bond and the other ==== is a single bond;
m is an integer between 1 and 10; and
n is an integer between 1 and 100,000.

Unless otherwise defined, all technical and scientific terms used herein have the same meaning as commonly understood by one of ordinary skill in the art to which this application belongs. In the specification, the singular forms also include the plural unless the context clearly dictates otherwise. Although methods and materials similar or equivalent to those described herein can be used in the practice or testing of the present application, suitable methods and materials are described below. In addition, the materials, methods, and examples are illustrative only and are not intended to be limiting.

Other features and advantages of the application will be apparent from the following detailed description and claims.

DETAILED DESCRIPTION

Figure 1:
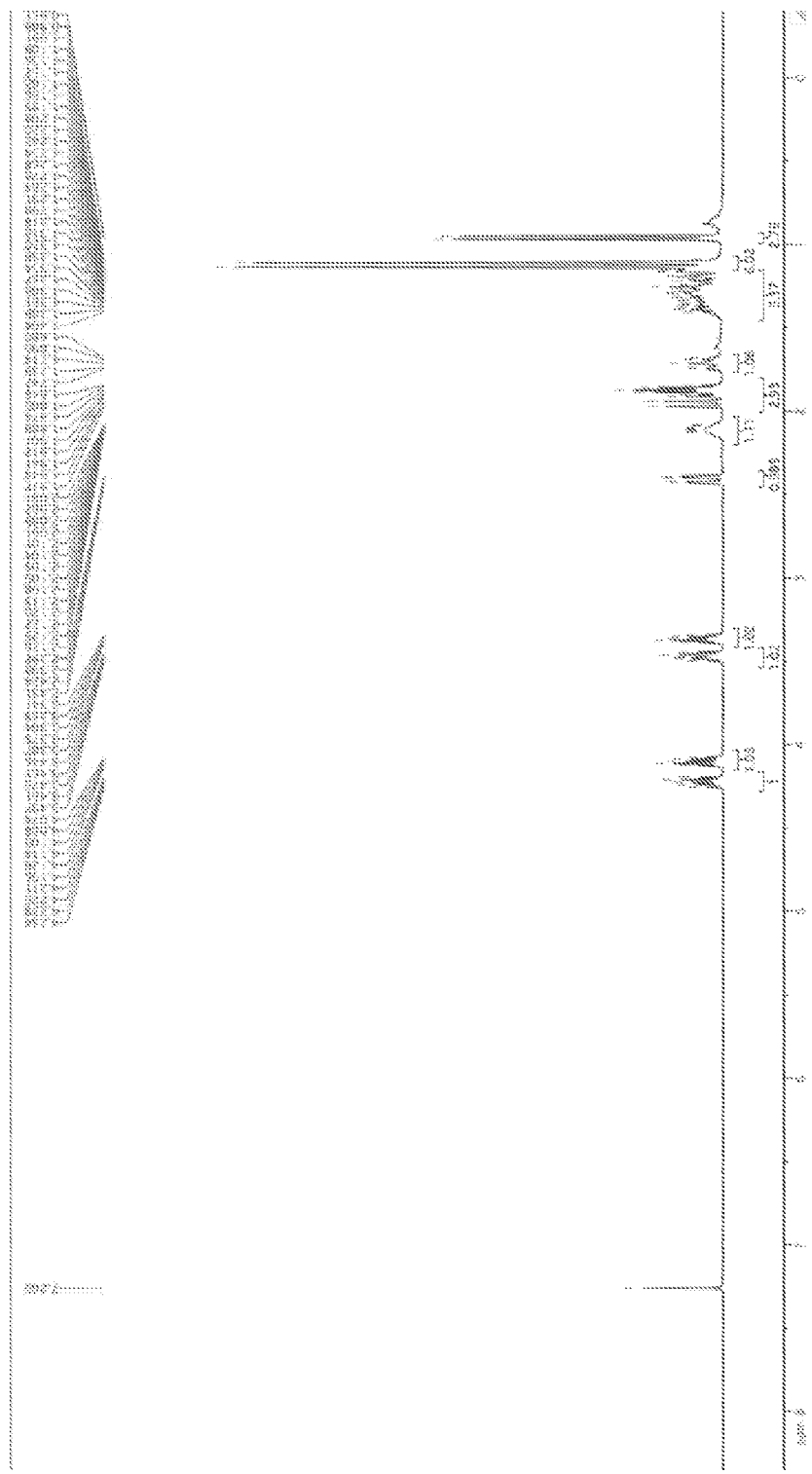
FIG. 1 is a $^1$H NMR spectrum of 8,12,12-trimethyl-1,5-dioxacyclododecan-6-one.

In one aspect, the application features a compound according to Formula I or Formula II:

Formula I

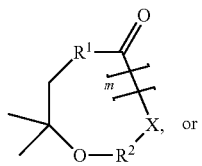

Formula II

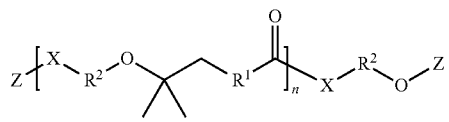

or a salt thereof, wherein,
R$^1$ is a bond, optionally substituted C$_1$-C$_{12}$ alkyl, optionally substituted C$_2$-C$_{12}$ alkenyl, or optionally substituted C$_2$-C$_{12}$ alkynyl;
R$^2$ is optionally substituted C$_1$-C$_{12}$ alkyl, optionally substituted C$_2$-C$_{12}$ alkenyl, or optionally substituted C$_2$-C$_{12}$ alkynyl;

X is O or NR$^x$;
R$^x$ is hydrogen or optionally substituted C$_1$-C$_{12}$ alkyl;
Z is hydrogen or

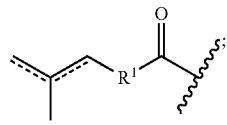

one of the ==== is a double bond and the other ==== is a single bond;
m is an integer between 1 and 10; and
n is an integer between 1 and 100,000.

In some embodiments, the compound is a compound according to Formula I.
In some embodiments, the compound is a compound according to Formula II.
In some embodiments, the number of atoms comprising the ring structure of Formula I is between 10 and 30.
In some embodiments, the number of atoms comprising the ring structure of Formula I is between 13 and 19.
In some embodiments, the number of atoms comprising the ring structure of Formula I is greater than 30.
In embodiments, the number of atoms comprising the ring structure of Formula I does not include exocyclic atoms such as an oxygen atom attached to a ring-forming carbon atom of a carbonyl group.
In some embodiments, X is O.
In some embodiments, X is NR$^x$.
In some embodiments, X is NH.
In some embodiments, Z is hydrogen.
In some embodiments, Z is

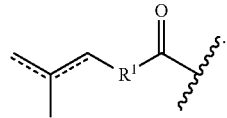

In some embodiments, each R$^1$ independently is optionally substituted linear C$_1$-C$_{12}$ alkyl or branched C$_3$-C$_{12}$ alkyl.
In some embodiments, each R$^1$ independently is unsubstituted linear C$_1$-C$_{12}$ alkyl or branched C$_3$-C$_{12}$ alkyl.
In some embodiments, each R$^1$ independently is unsubstituted linear C$_1$-C$_{12}$ alkyl.
In some embodiments, each R$^1$ independently is unsubstituted branched C$_3$-C$_{12}$ alkyl.
In some embodiments, each R$^1$ independently is optionally substituted linear C$_2$-C$_{12}$ alkenyl or branched C$_3$-C$_{12}$ alkenyl.
In some embodiments, each R$^1$ independently is unsubstituted linear C$_2$-C$_{12}$ alkenyl or branched C$_3$-C$_{12}$ alkenyl.
In some embodiments, each R$^1$ independently is unsubstituted linear C$_2$-C$_{12}$ alkenyl.
In some embodiments, each R$^1$ independently is unsubstituted branched C$_3$-C$_{12}$ alkenyl.
In some embodiments, each R$^2$ independently is optionally substituted linear or branched C$_3$-C$_{12}$ alkyl.
In some embodiments, each R$^2$ independently is linear C$_1$-C$_{12}$ alkyl or branched C$_3$-C$_{12}$ alkyl substituted with one or more hydroxyl groups.
In some embodiments, each R$^2$ independently is unsubstituted linear C$_1$-C$_{12}$ alkyl or branched C$_3$-C$_{12}$ alkyl.

In some embodiments, each $R^2$ independently is unsubstituted linear $C_1$-$C_{12}$ alkyl.

In some embodiments, each $R^2$ independently is unsubstituted branched $C_3$-$C_{12}$ alkyl.

In some embodiments, each $R^2$ independently is optionally substituted linear $C_2$-$C_{12}$ alkenyl or branched $C_3$-$C_{12}$ alkenyl.

In some embodiments, each $R^2$ independently is unsubstituted linear $C_2$-$C_{12}$ alkenyl or branched $C_3$-$C_{12}$ alkenyl.

In some embodiments, each $R^2$ independently is unsubstituted linear $C_2$-$C_{12}$ alkenyl.

In some embodiments, each $R^2$ independently is unsubstituted branched $C_3$-$C_{12}$ alkenyl.

In some embodiments, each $R^2$ independently is optionally substituted linear $C_2$-$C_{12}$ alkynyl or branched $C_4$-$C_{12}$ alkynyl.

In some embodiments, each $R^2$ independently is unsubstituted linear $C_2$-$C_{12}$ alkynyl or branched $C_4$-$C_{12}$ alkynyl.

In some embodiments, each $R^2$ independently is unsubstituted linear $C_2$-$C_{12}$ alkynyl.

In some embodiments, each $R^2$ independently is unsubstituted branched $C_4$-$C_{12}$ alkynyl.

In some embodiments, the compound of Formula II is selected from those listed in Table 2 and salts thereof.

In some embodiments, the compound of Formula I is selected from those listed in Table 3 and salts thereof.

In some embodiments, n is greater than 1 (e.g., between 2 and about 100, between about 100 and about 1,000, between about 1,000 and about 5,000, between about 5,000 and about 10,000, between about 10,000 and about 50,000, between about 50,000 and about 100,000, between about 10 and about 100,000, between about 100 and about 10,000, between about 200 and about 20,000, or between about 500 and about 50,000).

In some embodiments, the compound of Formula II has a molecular weight of about 5000 Da or greater.

In some embodiments, m is 1 or 2.

In some embodiments, m is 3, 4, 5, 6, 7, 8, 9, or 10.

In another aspect, the application features a method of producing a compound of Formula I and/or Formula II, or a salt, or a combination thereof, comprising reacting a compound of Formula III or Formula IV:

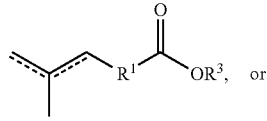

Formula III

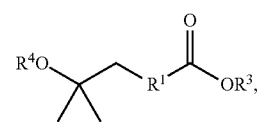

Formula IV with a compound of Formula V:

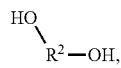

Formula V to obtain a reaction mixture comprising a compound of Formula I or Formula II, a salt thereof, or a combination thereof:

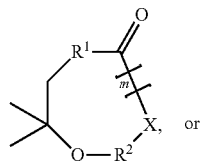

Formula I

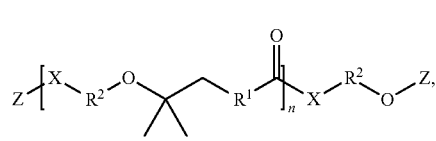

Formula II wherein, $R^1$ is a bond, optionally substituted $C_1$-$C_{12}$ alkyl, optionally substituted $C_2$-$C_{12}$ alkenyl, or optionally substituted $C_2$-$C_{12}$ alkynyl;

$R^2$ is optionally substituted $C_1$-$C_{12}$ alkyl, optionally substituted $C_2$-$C_{12}$ alkenyl, or optionally substituted $C_2$-$C_{12}$ alkynyl;

$R^3$ is hydrogen, optionally substituted $C_1$-$C_{12}$ alkyl, optionally substituted $C_2$-$C_{12}$ alkenyl, or optionally substituted $C_2$-$C_{12}$ alkynyl;

$R^4$ is hydrogen, optionally substituted $C_1$-$C_{12}$ alkyl, optionally substituted $C_2$-$C_{12}$ alkenyl, or optionally substituted $C_2$-$C_{12}$ alkynyl;

X is O or $NR^x$;

$R^x$ is hydrogen or optionally substituted $C_1$-$C_{12}$ alkyl;

Z is hydrogen or

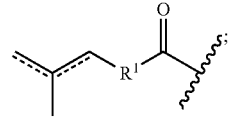

one of the ==== is a double bond and the other ==== is a single bond;

m is an integer between 1 and 10; and n is an integer between 1 and 100,000.

In some embodiments, the reaction of a compound of Formula III or Formula IV with a compound of Formula V comprises an esterification step, an etherification step, a first distillation step, and a second distillation step.

In some embodiments, water is removed from the reaction mixture during the esterification step.

In some embodiments, the method further comprises an amidation step, wherein a compound of Formula I, wherein X is O, reacts with $NH_3$ under an elevated pressure to obtain a corresponding compound of Formula I wherein X is NH.

In some embodiments, the ratio of the compound of Formula III or Formula IV to the compound of Formula V is 2 to 1 or greater (e.g., about 3 to 1, 4 to 1, 5 to 1, 6 to 1, 8 to 1, or 10 to 1).

In some embodiments, the esterification step is performed at a first temperature that is greater than room temperature.

In some embodiments, the first temperature is about 130° C.

In some embodiments, the esterification step is performed at a first pH value that is less than or equal to 7.

In some embodiments, the first pH value is less than 7.

In some embodiments, the esterification step is performed for less than 4 hours.

In some embodiments, the esterification step is performed for about 4 hours.

In some embodiments, the esterification step is performed for greater than 4 hours (e.g., about 5-24 hours).

In some embodiments, the etherification step is performed at a second temperature that is lower than the first temperature.

In some embodiments, the second temperature is about 65° C.

In some embodiments, the etherification step is performed at a second pH value that is greater than or equal to the first pH.

In some embodiments, the second pH value of the etherification step is greater than or equal to 7.

In some embodiments, the etherification step is quenched with a base, e.g., $Na_2CO_3$.

In some embodiments, the etherification step is quenched with $Na_2CO_3$, such that the pH of the reaction mixture is about 8.

In some embodiments, the etherification step is performed for less than 48 hours.

In some embodiments, the etherification step is performed for about 48 hours.

In some embodiments, the etherification step is performed for greater than 48 hours (e.g., about 50-120 hours).

In some embodiments, the first distillation step is performed to remove the compound of Formula V from the reaction mixture.

In some embodiments, the compound of Formula I is separated from the compound of Formula II by performing a second distillation step.

In some embodiments, each of the first and second distillation steps is independently performed at a third temperature that is between about 25° C. and about 280° C. (e.g., about 25-270° C., 25-260° C., 30-120° C., 30-150° C., 30-200° C., 100-150° C., 150-270° C., or about 200-270° C.).

In some embodiments, each of the first and second distillation steps is independently performed at a pressure between 0.01 mbar and 10 mbar, (e.g., between 0.05 mbar and 5 mbar, between 0.1 mbar and 3 mbar, between 0.1 and 0.3 mbar, between 0.3 and 0.5 mbar, between 0.5 and 1.0 mbar, or between 1.0 and 1.6 mbar).

In some embodiments, the first distillation step is performed at a temperature from 25° C. to 260° C. (e.g., from 25° C. to 250° C.) under a pressure of 0.5-2.0 mbar (e.g., 0.5-1.0 mbar or 1.0-1.6 mbar).

In some embodiments, the second distillation step is performed at a temperature at 200-270° C. (e.g., 200-260° C.). under a pressure of 0.5-1.0 mbar (e.g., 0.1-0.5 mbar or 0.3-0.5 mbar).

In some embodiments, $R^3$ is hydrogen.

In some embodiments, $R^3$ is optionally substituted linear $C_1$-$C_{12}$ alkyl or branched $C_3$-$C_{12}$ alkyl.

In some embodiments, $R^3$ is unsubstituted linear $C_1$-$C_{12}$ alkyl or branched $C_3$-$C_{12}$ alkyl.

In some embodiments, $R^3$ is unsubstituted linear $C_1$-$C_{12}$ alkyl.

In some embodiments, $R^3$ is unsubstituted branched $C_3$-$C_{12}$ alkyl.

In some embodiments, $R^4$ is hydrogen.

In some embodiments, $R^4$ is optionally substituted linear $C_1$-$C_{12}$ alkyl or branched $C_3$-$C_{12}$ alkyl.

In some embodiments, $R^4$ is unsubstituted linear $C_1$-$C_{12}$ alkyl or branched $C_3$-$C_{12}$ alkyl.

In some embodiments, $R^4$ is unsubstituted linear $C_1$-$C_{12}$ alkyl.

In some embodiments, $R^4$ is unsubstituted branched $C_3$-$C_{12}$ alkyl.

In addition to making the macrocyclic compounds of Formula I, the process described herein may be used to generate the polymers of Formula II. Such polymers can be used for a variety of application, including cosmetics, coatings, medical devices, and time-release formulations, as well as any other appropriate polymer applications. These new polymers can contain either alternating ether/ester linkages, or ether/amide linkages.

The polymers described herein (of Formula II) can be used as precursors to produce macrocyclic compounds (of Formula I) that contain an ether linkage. As an example, and as illustrated in Scheme 1 below, polymers can be formed by esterifying and etherifying an olefinic acid and/or ester (e.g., compound 1a or 1b in Scheme 1) with a suitable diol of the type described in Scheme 1 (e.g., compound 2) under suitable conditions (e.g., acidic conditions; e.g., elevated temperatures; e.g., reaction times ranging from hours to days). The resulting monomer (e.g., compound 3) can then be polymerized to form a polymer (e.g., compound 5) (e.g., under vacuum distillation conditions) in the presence of a suitable catalyst, such as a basic catalyst (e.g., potassium carbonate, sodium carbonate, magnesium oxide, or basic alumina). The extent to which the diol (compound 2) is removed from the reaction mixture can influence the polymerization reaction. In one embodiment, the amount of diol (compound 2) removed from the reaction mixture (e.g., by distillation) is inversely proportional to the average molecular weight of the polymer product. The macrocyclic compound (e.g., compound 4) can be separated from the reaction mixture (e.g., by distillation) upon depolymerization/lactonization of the polymer (compound 5), which occurs via the intramolecular esterification of a terminal hydroxyl group with an internal ester group. The resulting polymer (compound 5) is a new type of ester/ether polymer, and the resulting macrocyclic compound (compound 4) is a new type of ester/ether macrocycle. The variables in Scheme 1 below, such as $R^1$, $R^2$, X, Z, etc. are as defined in Formulae I-V above.

Scheme 1

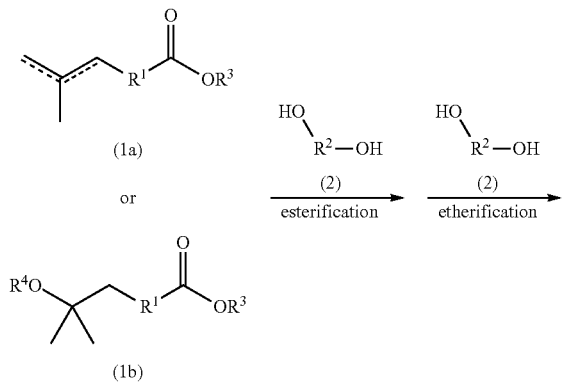

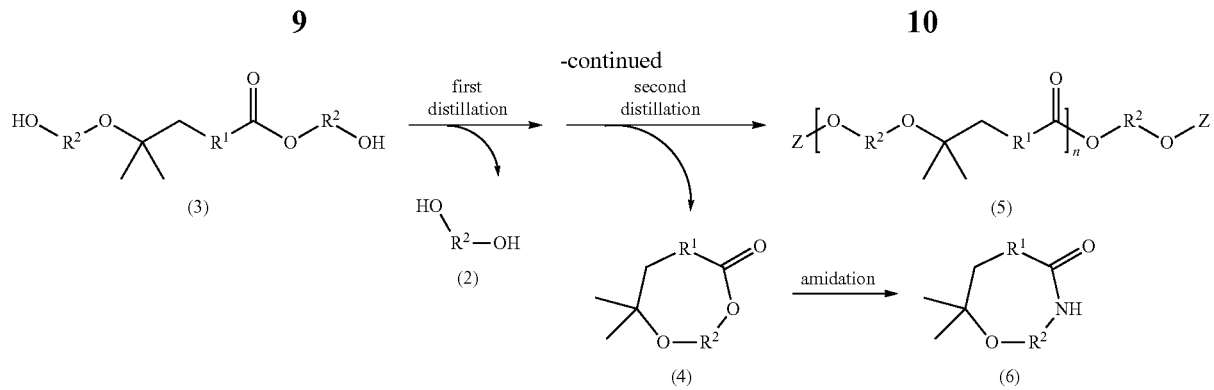

In some embodiments, an esterification procedure may occur before, concurrently with, or after an etherification procedure. In some embodiments, polymerization and/or lactonization reactions may occur during a first and/or second distillation procedure. In some embodiments, a compound of Formula II (e.g., compound 5 in Scheme 1) may be isolated from the reaction mixture in a first or a second distillation procedure. In some embodiments, a compound of Formula I wherein X is O (e.g., compound 4 in Scheme 1) may be reacted with pressurized ammonia to produce a corresponding compound of Formula I wherein X is NH (e.g., compound 6 in Scheme 1).

In some embodiments, 2,6-dimethyl-6-methoxyheptanoic acid is combined with 1,6-hexanediol and methanesulfonic acid in an organic solvent (e.g., toluene) and heated, to 25° C.-200° C. (e.g., to 25° C., e.g., to 50° C., e.g., to 75° C., e.g., to 100° C., e.g., to 110° C., e.g., to 120° C., e.g., to 130° C., e.g., to 140° C., e.g., to 150° C., e.g., to 160° C., e.g., to 180° C., e.g., to 200° C.), for 0.5-10 hours (e.g., 0.5 hours, e.g., 1 hour, e.g., 2 hours, e.g., 3 hours, e.g., 4 hours, e.g., 5 hours, e.g., 6 hours, e.g., 8 hours, e.g., 10 hours) to perform the esterification step. The reaction is then cooled, to 25° C.-100° C. (e.g., to 20-30° C., e.g., to 30-40° C., e.g., to 40-50° C., e.g., to 50-60° C., e.g., to 60-70° C., e.g., to 70-80° C., e.g., to 80-90° C., e.g., to 90-100° C.) and additional 1,6-hexanediol is added to the reaction mixture to perform the etherification step. The reaction is kept stirring at the cooled temperature for, 1 hour to 4 days (e.g., 1 hour, e.g., 6 hours, e.g., 12 hours, e.g., 1 day, e.g., 2 days, e.g., 3 days, e.g., 4 days) before quenching the reaction with a basic aqueous solution (e.g., 10 wt. % Na$_2$CO$_3$) until the pH of the reaction mixture is slightly basic (e.g., pH=8). A polar organic solvent (e.g., ethyl acetate) is added to reaction mixture and the phases are separated. The organic phase is washed with brine and then dried with a drying agent (e.g., Na$_2$SO$_4$). The drying agent is removed by filtration, and the organic phase solvent is subsequently removed by evaporation, yielding a residue. An inorganic catalyst (e.g., MgO) and quenching agent (e.g., Na$_2$CO$_3$) are added to the residue, and fractional distillation is performed (the first distillation). After removing a majority of the light fraction, the macrolactone product is removed from the remaining reaction mixture by distillation (the second distillation). The macrolactone product may be further purified (e.g., by flash column chromatography). Residue in the reaction vessel after distillation includes polymer (e.g., poly(11,15,15-trimethyl-1,8-dioxacyclopentadecan-9-one)). Product compositions and yields are determined by e.g., NMR.

In some embodiments, citronellic acid is combined with 1,3-propanediol and methanesulfonic acid in an organic solvent (e.g., toluene) and heated, to 25° C.-200° C. (e.g., to 25° C., e.g., to 50° C., e.g., to 75° C., e.g., to 100° C., e.g., to 110° C., e.g., to 120° C., e.g., to 130° C., e.g., to 140° C., e.g., to 150° C., e.g., to 160° C., e.g., to 180° C., e.g., to 200° C.) for 0.5-10 hours (e.g., 0.5 hours, e.g., 1 hour, e.g., 2 hours, e.g., 3 hours, e.g., 4 hours, e.g., 5 hours, e.g., 6 hours, e.g., 8 hours, e.g., 10 hours), during which water is removed from the reaction, to perform the esterification step. The reaction is then cooled, to 25° C.-100° C. (e.g., to 20-30° C., e.g., to 30-40° C., e.g., to 40-50° C., e.g., to 50-60° C., e.g., to 60-70° C., e.g., to 70-80° C., e.g., to 80-90° C., e.g., to 90-100° C.) and left stirring, for 1 hour-4 days (e.g., 1 hour, e.g., 6 hours, e.g., 12 hours, e.g., 1 day, e.g., 2 days, e.g., 3 days, e.g., 4 days), to perform the etherification step, before quenching the reaction with a basic aqueous solution (e.g., 10% Na$_2$CO$_3$) until the pH of the reaction mixture is slightly basic (e.g., pH=8). A polar organic solvent (e.g., ethyl acetate) is added to reaction mixture and the phases are separated. The organic phase is washed with brine and then dried with a drying agent (e.g., Na$_2$SO$_4$). The drying agent is removed by filtration and the solvent is removed by evaporation, yielding a residue. An inorganic catalyst (e.g., MgO) and quenching agent (e.g., Na$_2$CO$_3$) are added to the residue, and fractional distillation is performed (the first distillation). After removing a majority of the light fraction, the macrolactone product is isolated from the remaining reaction mixture by distillation (the second distillation). The macrolactone product may be further purified e.g., by flash column chromatography. Residue in the reaction vessel after distillation includes polymer (e.g., poly(11,15,15-trimethyl-1,8-dioxacyclopentadecan-9-one)). Product compositions and yields are determined e.g., by NMR.

In some embodiments, citronellic acid is combined with ethylene glycol and methanesulfonic acid in an organic solvent (e.g., toluene) and heated, to 25° C.-200° C. (e.g., to 25° C., e.g., to 50° C., e.g., to 75° C., e.g., to 100° C., e.g., to 110° C., e.g., to 120° C., e.g., to 130° C., e.g., to 140° C., e.g., to 150° C., e.g., to 160° C., e.g., to 180° C., e.g., to 200° C.) for 0.5-10 hours (e.g., 0.5 hours, e.g., 1 hour, e.g., 2 hours, e.g., 3 hours, e.g., 4 hours, e.g., 5 hours, e.g., 6 hours, e.g., 8 hours, e.g., 10 hours), during which water is removed from the reaction, to perform the esterification step. The reaction is then cooled, to 25° C.-100° C. (e.g., to 20-30° C., e.g., to 30-40° C., e.g., to 40-50° C., e.g., to 50-60° C., e.g., to 60-70° C., e.g., to 70-80° C., e.g., to 80-90° C., e.g., to 90-100° C.) and left stirring, for 1 hour-4 days (e.g., 1 hour, e.g., 6 hours, e.g., 12 hours, e.g., 1 day, e.g., 2 days, e.g., 3 days, e.g., 4 days), to perform the etherification step, before quenching the reaction with a basic aqueous solution (e.g., 10% Na$_2$CO$_3$) until the pH of the reaction mixture is slightly basic (e.g., pH=8). A polar organic solvent (e.g., ethyl acetate) is added to reaction mixture and the phases are separated. The organic phase is washed with brine and then dried with a drying agent (e.g., Na$_2$SO$_4$). The drying agent is removed by filtration and the solvent is removed by evaporation, yielding a residue. An inorganic catalyst (e.g., MgO) and quenching agent (e.g., Na$_2$CO$_3$) are added to the residue, and fractional distillation is performed (first distillation). After removing a majority of the light fraction, the macrolactone product is removed from the remaining reaction mixture by distillation (second distillation). The macrolactone product may be further purified e.g., by flash column chromatography. Residue in the reaction vessel after distillation includes polymer (e.g., poly(7-(2-hydroxyethoxy)-3,7-dimethyloctanoic acid)). Product compositions and yields are determined e.g., by NMR.

The process described herein can be applied using many different combinations of olefinic acids or esters and diols, resulting in a large variety of new compositions of matter. Further, the olefinic acids and esters can be etherified or hydroxylated at the most highly substituted carbon of the olefin and used as a functional equivalent to the olefin. For example, Scheme 2 shows three functional equivalents for this process, where R$^1$, R$^3$, and R$^4$ are as defined in Formula III above.

Scheme 2

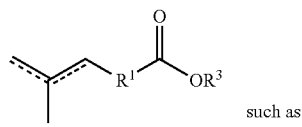

such as

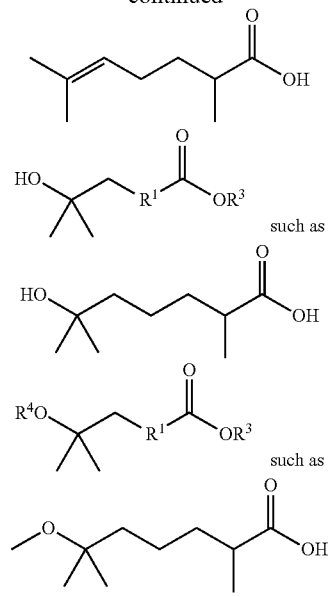

Non-limiting examples of suitable olefinic acids and esters for the processes described herein include those depicted in Table 1 below, as well as their substituted and/or unsaturated analogs and functional equivalents. One of the ==== is a double bond and the other ==== is a single bond, and R$^3$ is as defined in Formula III above.

TABLE 1

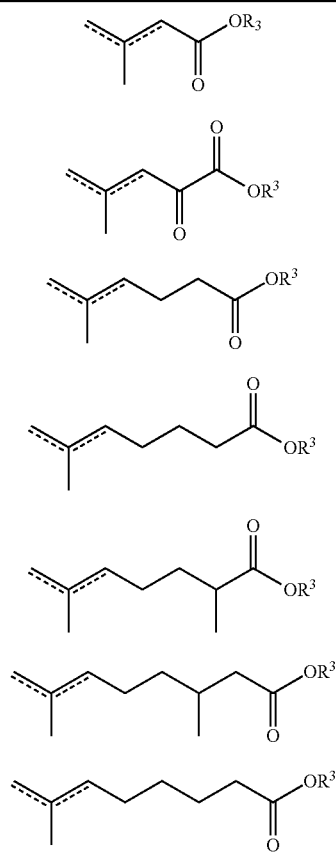

TABLE 1-continued

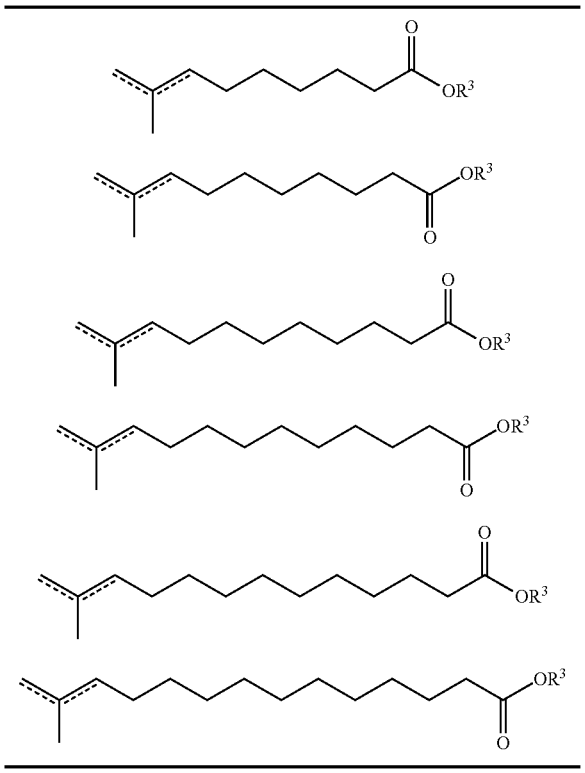

Several of the molecules in Table 1, above, can be derived from renewable resources such as terpenes (e.g., citronellic acid and/or citronellenes) or unsaturated vegetable oil fatty acids. When obtaining these molecules from unsaturated fatty acids, metathesis of the fatty acids with a suitable olefin such as isobutylene or 2,3-dimethylbutene, or reductive ozonolysis followed by Wittig-type olefination, may yield suitable starting materials. Metathesis of fatty acids may also give rise to internal olefins that can then undergo olefin isomerization to produce compounds of the type described in Table 1. In general, the olefins and corresponding functional equivalents can also be made by adding organometallic species to esters, performing Wittig- or Homer-Wadsworth-Emmons-type olefinations of aldehydes, or by performing metathesis reactions on suitable olefin precursors.

Suitable diols for the process described herein include, e.g., ethylene glycol, propylene glycol, erythritol, pentaerythiritol, sorbitol, 1,3-propanediol, glycerol, 1,4-butanediol, 1,4-butenediol, 1,4-butynediol, 1,5-pentanediol, 1,6, hexanediol, 1,6-hexenediol, 1,6-hexynediol, 1,7-heptanediol, 1,8-octanediol, 1,9-nonanediol, 1,10-decanediol, 1,11-dodecanediol, 1,12-doedecanediol, 1,13-tridecanediol, 1,14-tetradecanediol, 1,15-pentadecanediol, and 1,16-hexadecanediol, as well as their substituted, polymeric, and/or unsaturated analogs. Diols that are removed from the reaction mixtures described herein by distillation can be reused.

The polymers obtained from this process may possess olefinic terminal groups, as described in Scheme 1 and as indicated in Formula II. These olefinic groups can be used to further grow the polymer and add additional functionality. Methods to prepare and grow olefinic polymers include free radical polymerization, metathesis polymerization, anionic polymerization, and/or cationic polymerization. Table 2 below includes representative polymers that can be obtained by the processes described herein, where n is as defined in Formula II above.

TABLE 2

| COMPOUND NUMBER | STRUCTURE |
| --- | --- |
| 603 | 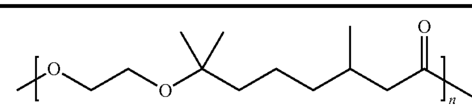 |
| 604 | 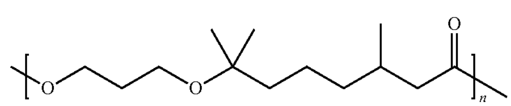 |
| 606 | 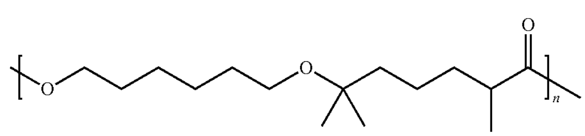 |
| 610 | 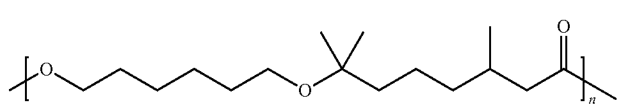 |
| 703 | 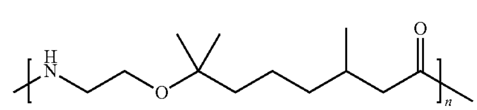 |
| 704 | 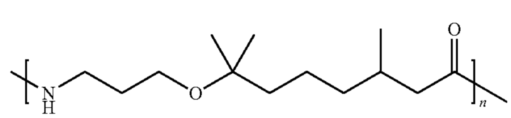 |

TABLE 2-continued

| COMPOUND NUMBER | STRUCTURE |
| --- | --- |
| 706 | 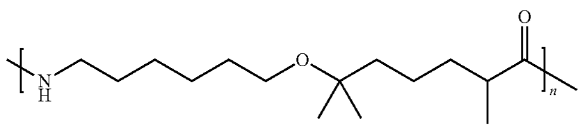 |
| 710 | 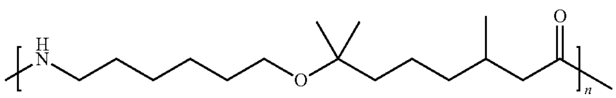 |

Representative macrocyclic compounds that can be obtained from the processes described herein are shown in Table 3.

TABLE 3

| COMPOUND NUMBER | STRUCTURE |
| --- | --- |
| 101 | 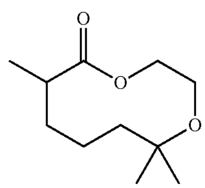 |
| 102 | 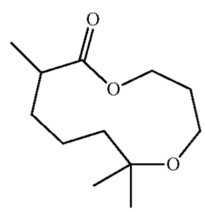 |
| 103 | 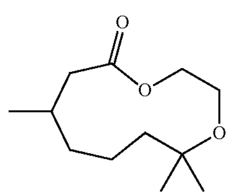 |
| 104 | 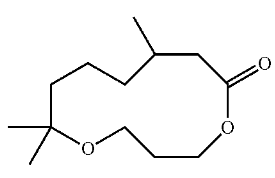 [SMILES: CC1CCCC(C)(C)OCCCOC(=O)C1] |
| 105 | 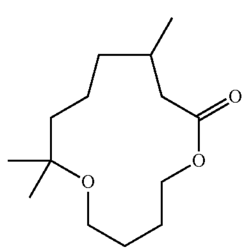 [SMILES: CC1CCCC(C)(C)OCCCCOC(=O)C1] |

TABLE 3-continued

| COMPOUND NUMBER | STRUCTURE |
|---|---|
| 106 | 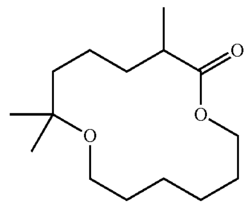 [SMILES: CC1CCCC(C)(C)OCCCCCCOC1=O] |
| 107 | 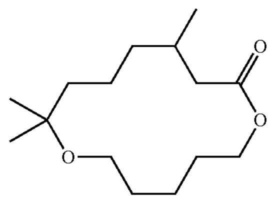 [SMILES: CC1CCCC(C)(C)OCCCCCOC(=O)C1] |
| 108 | 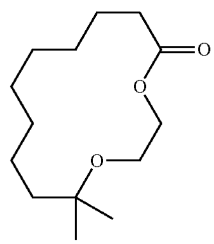 [SMILES: CC1(C)CCCCCCCCC(=O)OCCO1] |
| 109 | 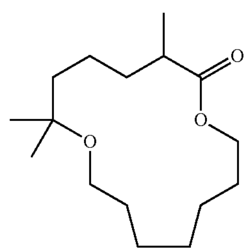 [SMILES: CC1CCCC(C)(C)OCCCCCCCOC1=O] |
| 110 | 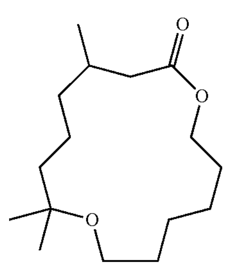 [SMILES: CC1CCCC(C)(C)OCCCCCCOC(=O)C1] |
| 111 | 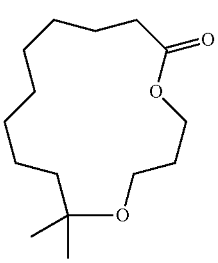 [SMILES: CC1(C)CCCCCCCCC(=O)OCCCO1] |

TABLE 3-continued
| COMPOUND NUMBER | STRUCTURE |
|---|---|
| 112 | 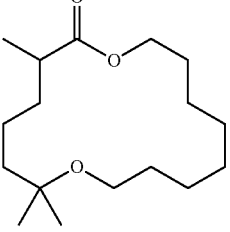 |
| 113 | 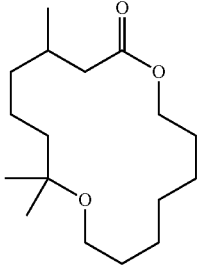 [SMILES: CC1CCCC(C)(C)OCCCCCCCOC(=O)C1] |
| 114 | 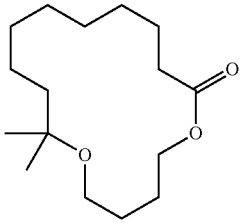 [SMILES: CC1(C)CCCCCCCCC(=O)OCCCCO1] |
| 115 | 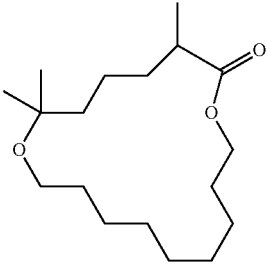 [SMILES: CC1CCCC(C)(C)OCCCCCCCCCOC1=O] |
| 116 | 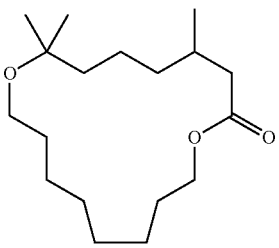 [SMILES: CC1CCCC(C)(C)OCCCCCCCCOC(=O)C1] |
| 117 | 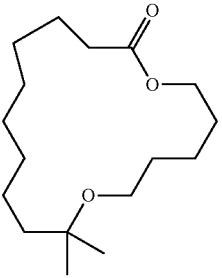 [SMILES: CC1(C)CCCCCCCCC(=O)OCCCCCO1] |

TABLE 3-continued

| COMPOUND NUMBER | STRUCTURE |
| --- | --- |
| 118 | 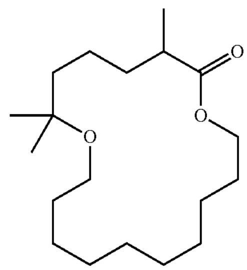 [SMILES: CC1CCCC(C)(C)OCCCCCCCCCCOC1=O] |
| 119 | 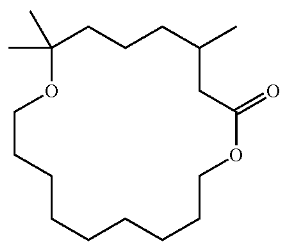 [SMILES: CC1CCCC(C)(C)OCCCCCCCCCOC(=O)C1] |
| 120 | 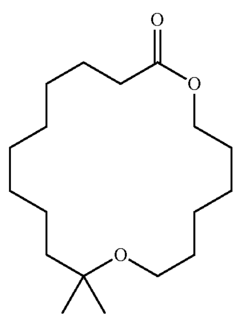 [SMILES: CC1(C)CCCCCCCCC(=O)OCCCCCCO1] |
| 121 | 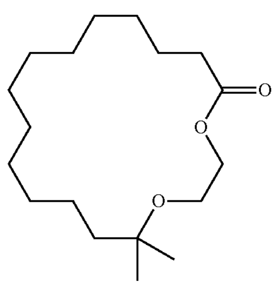 [SMILES: CC1(C)CCCCCCCCCCCCC(=O)OCCO1] |
| 122 | 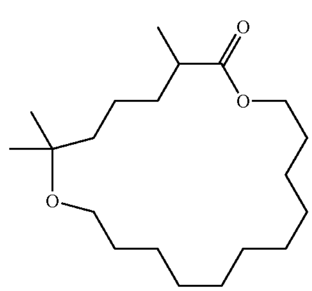 [SMILES: CC1CCCC(C)(C)OCCCCCCCCCCCOC1=O] |

TABLE 3-continued
| COMPOUND NUMBER | STRUCTURE |
| --- | --- |
| 123 | 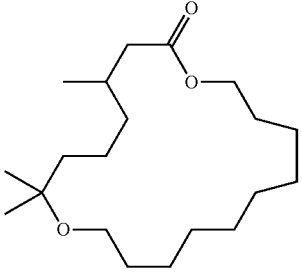 [SMILES: CC1CCCC(C)(C)OCCCCCCCCCCOC(=O)C1] |
| 124 | 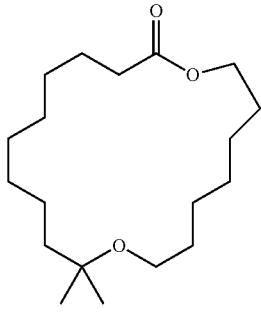 [SMILES: CC1(C)CCCCCCCCC(=O)OCCCCCCCO1] |
| 125 | 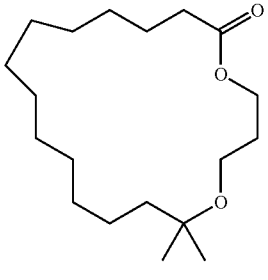 [SMILES: CC1(C)CCCCCCCCCCCCC(=O)OCCCO1] |
| 205 | 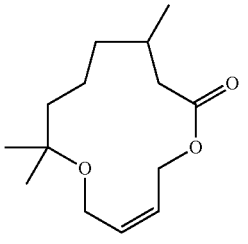 [SMILES: CC1CCCC(C)(C)OC/C=C\COC(=O)C1] |
| 206 | 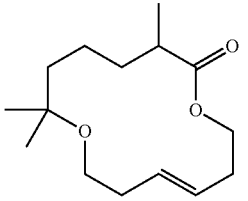 [SMILES: CC1CCCC(C)(C)OCC/C=C/CCOC1=O] |
| 207 | 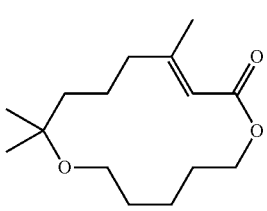 [SMILES: C/C1=C\C(=O)OCCCCCOC(C)(C)CCC1] |

TABLE 3-continued
| COMPOUND NUMBER | STRUCTURE |
|---|---|
| 210 | 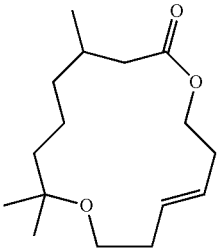 [SMILES: CC1CCCC(C)(C)OCC/C=C/CCOC(=O)C1] |
| 214 | 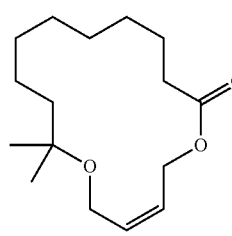 |
| 216 | 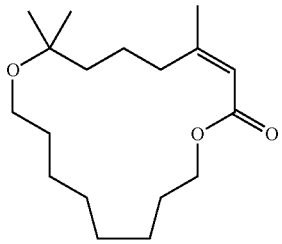 [SMILES: C/C1=C/C(=O)OCCCCCCCCOC(C)(C)CCC1] |
| 219 | 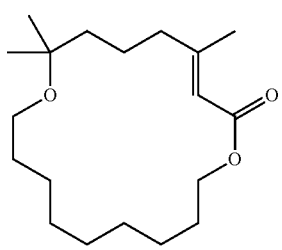 [SMILES: C/C1=C\C(=O)OCCCCCCCCCOC(C)(C)CCC1] |
| 220 | 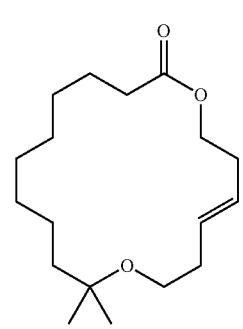 [SMILES: CC1(C)CCCCCCCCC(=O)OCC/C=C/CCO1] |
| 223 | 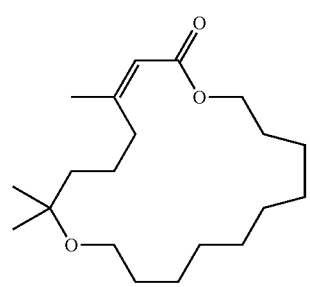 [SMILES: C/C1=C/C(=O)OCCCCCCCCCCOC(C)(C)CCC1] |

TABLE 3-continued

| COMPOUND NUMBER | STRUCTURE |
|---|---|
| 305 | 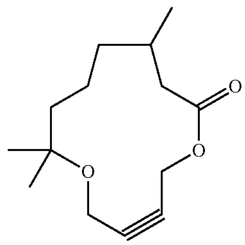 [SMILES: CC1CCCC(C)(C)OCC#CCOC(=O)C1] |
| 306 | 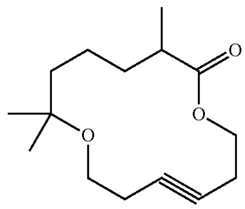 [SMILES: CC1CCCC(C)(C)OCCC#CCCOC1=O] |
| 310 | 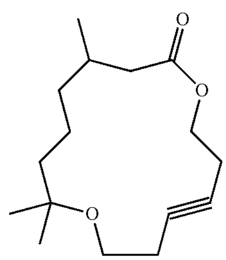 [SMILES: CC1CCCC(C)(C)OCCC#CCCOC(=O)C1] |
| 314 | 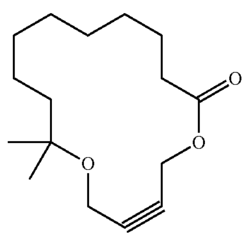 [SMILES: CC1(C)CCCCCCCCC(=O)OCC#CCO1] |
| 320 | 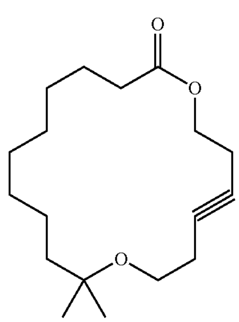 [SMILES: CC1(C)CCCCCCCCC(=O)OCCC#CCCO1] |
| 403 | 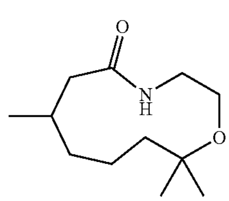 |

TABLE 3-continued
| COMPOUND NUMBER | STRUCTURE |
|---|---|
| 404 | 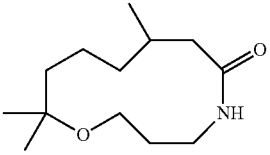 [SMILES: CC1CCCC(C)(C)OCCCNC(=O)C1] |
| 406 | 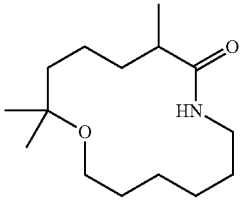 [SMILES: CC1CCCC(C)(C)OCCCCCCNC1=O] |
| 410 | 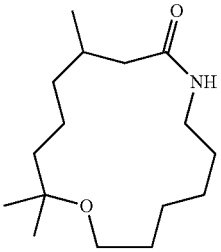 [SMILES: CC1CCCC(C)(C)OCCCCCCNC(=O)C1] |
| 806 | 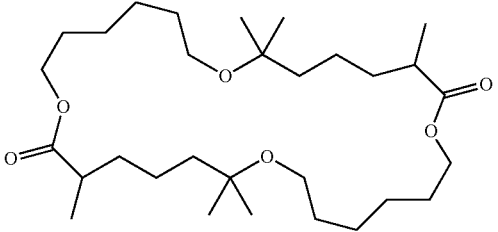 [SMILES: CC1CCCC(C)(C)OCCCCCCOC(=O)C(C)CCCC(C)(C)OCCCCCCOC1=O] |
| 810 | 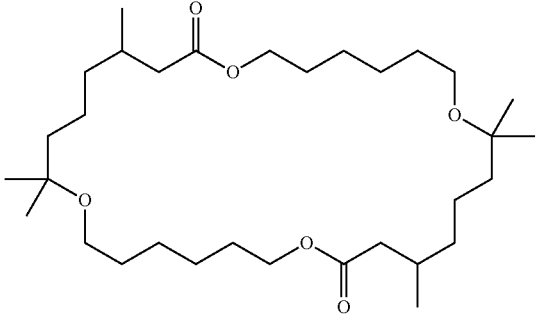 |

TABLE 3-continued

| COMPOUND NUMBER | STRUCTURE |
|---|---|
| 906 | (macrocyclic structure) |
| 910 | (macrocyclic structure) |

The macrocyclic compounds described herein can be used themselves, or as monomers for ring-opening polymerization. In some embodiments, an ester group oxygen atom of the macrocyclic compound of the application can be replaced with a nitrogen atom under high pressure with ammonia, thus allowing access to polyamide production (see e.g., Ritz, J., Fuchs, H., Kieczka, H. and Moran, W. C. 2011 Caprolactam. Ullmann's Encyclopedia of Industrial Chemistry). Scheme 3 below depicts a general synthesis route to convert macrocyclic ethers of the application to analogous macrocyclic amines and polyamines. The variables in Scheme 3 below, such as $R^1$, $R^2$, n, and Z, are as defined in Formulae I and II above.

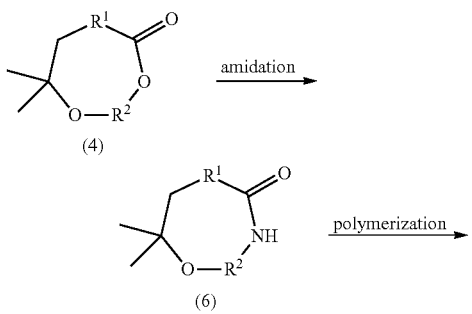

Scheme 3

-continued

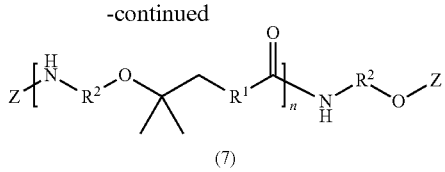

(7)

The details of one or more embodiments of the application are set forth in the accompanying description below. Unless defined otherwise, all technical and scientific terms used herein have the same meaning as commonly understood by one of ordinary skill in the art to which this application belongs. In the case of conflict, the present specification will control.

Unless otherwise indicated, it is to be understood that the terminology used herein is for the purpose of describing particular embodiments only and is not intended to be limiting. In this specification and in the claims that follow, reference will be made to a number of terms, which shall be defined to have the definitions set forth below.

As used herein, the singular forms "a," "an," and "the" include plural referents unless the context clearly dictates otherwise. Thus, for example, reference to "a reactant" includes not only a single reactant but also a combination or mixture of two or more different reactant, reference to "a substituent" includes a single substituent as well as two or more substituents, and the like.

As used herein, the phrases "for example," "for instance," "such as," or "including" are meant to introduce examples that further clarify more general subject matter. These examples are provided only as an aid for understanding the disclosure, and are not meant to be limiting in any fashion. Furthermore as used herein, the terms "may," "optional," "optionally," or "may optionally" mean that the subsequently described circumstance may or may not occur, so that the description includes instances where the circumstance occurs and instances where it does not. For example, the phrase "optionally present" means that an object may or may not be present, and, thus, the description includes instances wherein the object is present and instances wherein the object is not present.

As used herein, the phrase "having the formula" or "having the structure" is not intended to be limiting and is used in the same way that the term "comprising" is commonly used.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116). In some formulae of the present application, one or more chiral centers are identified by an asterisk placed next to the chiral carbon. In other formulae, no chiral center is identified, but the chiral isomers are nonetheless covered by these formulae.

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Some compounds of the present application can exist in a tautomeric form which is also intended to be encompassed within the scope of the present application. "Tautomers" refers to compounds whose structures differ markedly in arrangement of atoms, but which exist in easy and rapid equilibrium. It is to be understood that the compounds of the application may be depicted as different tautomers. It should also be understood that when compounds have tautomeric forms, all tautomeric forms are intended to be within the scope of the application, and the naming of the compounds does not exclude any tautomeric form. Further, even though one tautomer may be described, the present application includes all tautomers of the present compounds.

As used herein, the term "salt" can include acid addition salts including hydrochlorides, hydrobromides, phosphates, sulfates, hydrogen sulfates, alkylsulfonates, arylsulfonates, acetates, benzoates, citrates, maleates, fumarates, succinates, lactates, and tartrates; alkali metal cations such as $Na^+$, $K^+$, $Li^+$, alkali earth metal salts such as $Mg^{2+}$ or $Ca^{2+}$, or organic amine salts, or organic phosphonium salts.

The term "alkyl" as used herein refers to a monovalent or bivalent, branched or unbranched saturated hydrocarbon group typically although not necessarily containing 1 to about 12 carbon atoms, such as methyl, ethyl, n-propyl, isopropyl, n-butyl, isobutyl, t-butyl, octyl, and the like.

The term "alkenyl" as used herein refers to a monovalent or bivalent, branched or unbranched, unsaturated hydrocarbon group typically although not necessarily containing 2 to about 12 carbon atoms and 1-10 carbon-carbon double bonds, such as ethylene, n-propylene, isopropylene, n-butylene, isobutylene, t-butylene, octylene, and the like.

The term "alkynyl" as used herein refers to a monovalent or bivalent, branched or unbranched, unsaturated hydrocarbon group typically although not necessarily containing 2 to about 12 carbon atoms and 1-6 carbon-carbon triple bonds, such as ethyne, propyne, butyne, pentyne, hexyne, heptyne, octyne, and the like.

By "substituted" as in "substituted alkyl," "substituted alkenyl," "substituted alkynyl," and the like, it is meant that in the alkyl, alkenyl, alkynyl, or other moiety, at least one hydrogen atom bound to a carbon atom is replaced with one or more non-hydrogen substituents, e.g., by a functional group.

Examples of functional groups include, without limitation: halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—CO)—O-alkyl), $C_6$-$C_{20}$ aryloxycarbonyl (—CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—$NH_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—$NO_2$), nitroso (—NO), sulfo (—$SO_2$—OH), sulfonato (—$SO_2$—O), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)(O$^-$)$_2$), phosphinato (—P(O)(O$^-$)), phospho (—$PO_2$),-phosphino (—$PH_2$), mono- and di-($C_1$-$C_{24}$ alkyl)-substituted phosphino, mono- and di-($C_5$-$C_{20}$ aryl)-substituted phosphino; and the hydrocarbyl moieties such as $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). In addition, the aforementioned functional groups may, if a particular group permits, be further substituted with one or more additional functional groups or with one or more hydrocarbyl moieties such as those specifically enumerated above.

In the present specification, the structural formula of the compound represents a certain isomer for convenience in some cases, but the present application includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present application.

All percentages used herein, unless otherwise indicated, are by volume.

All ratios used herein, unless otherwise indicated, are by molarity.

EXAMPLES

Example 1: Synthesis of 3,7,7-trimethyl-1,8-dioxacyclotetradecan-2-one and its polymeric precursor

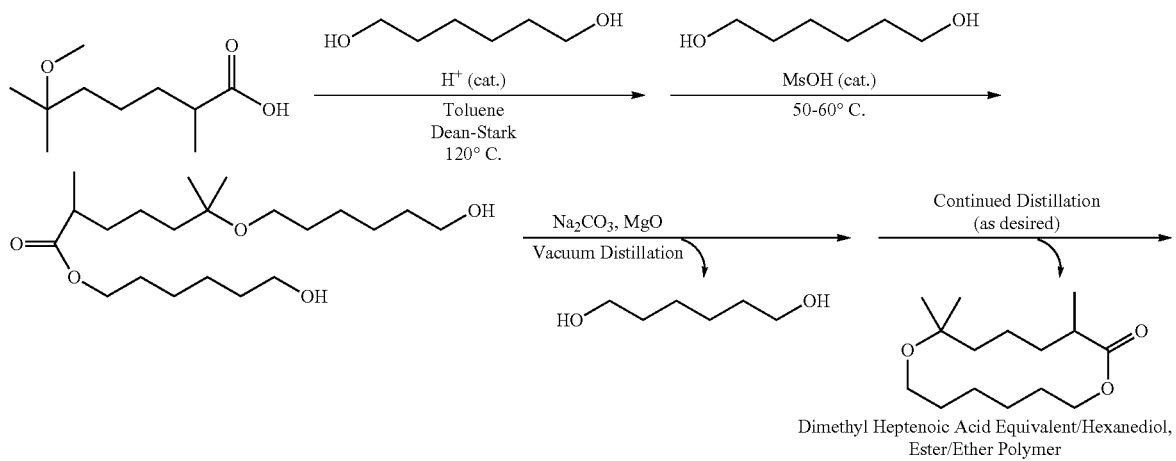

Dimethyl Heptenoic Acid Equivalent/Hexanediol, Ester/Ether Polymer

A mixture of 2,6-dimethyl-6-methoxyheptanoic acid (100 g, 0.53 mol), 1,6-hexanediol (125.5 g), methanesulfonic acid (10 g) and toluene (100 ml) in a 500 mL round bottom flask equipped with a Dean-Stark apparatus was heated at 120° C. for 4 hours, removing water formed in the Dean-Stark apparatus during the process. The reaction was cooled to 50-60° C. and additional 1,6-hexanediol (36 g) was added to the mixture. The reaction was then kept stirring at this temperature for 2 days before quenching the reaction with aqueous $Na_2CO_3$ (10% (w/v)) at room temperature (until pH=8). Ethyl acetate (100 ml) was added to the mixture and the phases were separated. The organic phase was washed with brine (150 ml) and then dried with $Na_2SO_4$. The $Na_2SO_4$ was filtered out and solvent was removed from the organic phase by evaporation, resulting in a red liquid residue (167 g). MgO (4 g) and $Na_2CO_3$ (4 g) were added to an aliquot of the residue (80 g) and fractional distillation was performed by heating the mixture from 25 to 250° C. under vacuum. After removing most of the light fraction at 1.0-1.6 mbar, the final fraction containing the macrolactone product was distilled from the remaining reaction mixture at 200-260° C. under 0.1-0.5 mbar vacuum. Purification of the final distillation fraction by flash column chromatography gave 2 g of macrolactone product (silica gel, 2-7.5% ethyl acetate/heptane). Residue in the reaction vessel after distillation (28 g) comprised poly(6-((6-hydroxyhexyl)oxy)-2,6-dimethyl-heptanoic acid), MgO, and $Na_2CO_3$. NMR spectra for the macrolactone and polymer products are described below.

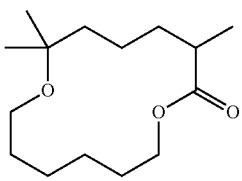

3,7,7-trimethyl-1,8-dioxacyclotetradecan-2-one

¹H NMR (CDCl₃, 400 MHz) δ 1.12 (s, 3H, —CH₃), 1.13 (s, 3H, —CH₃), 1.15 (d, J=7.2 Hz, 3H, —CH₃), 1.18-1.28 (m, 1H, —CH—), 1.34-1.75 (m, 13H, —CH₂—), 2.49-2.54 (m, 1H, —CH—), 3.24-3.32 (m, 2H, —CH₂O—), 4.05-4.11 (m, 1H, —CH₂O—), 4.13-4.19 (m, 1H, —CH₂O—). ¹³C NMR (100 MHz, CDCl₃) δ 17.4, 20.5, 23.7, 24.1, 26.5, 26.6, 28.2, 29.1, 34.8, 37.8, 40.4, 58.3, 63.1, 73.5, 176.4;

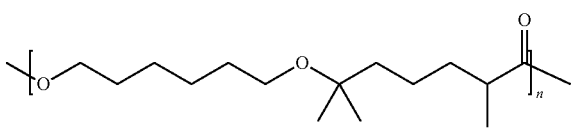

poly(6((6-hydroxyhexyl)oxy)-2,6-dimethylheptanoic acid), or alternatively, poly(3,7,7-trimethyl-1,8-dioxacyclotetradecan-2-one)

¹H NMR (CDCl₃, 400 MHz) δ 1.10 (s, 6H, —CH₃), 1.13 (d, J=6.8 Hz, 3H, —CH₃), 1.25-1.67 (m, 14H, —CH₂—), 2.39-2.44 (m, 1H, —CH—), 3.26 (t, 2H, J=6.4 Hz, —CH₂O—), 4.04 (t, 2H, J=6.4 Hz, —CH₂O—).

Example 2: Synthesis of 11,15,15-trimethyl-1,8-dioxacyclopentadecan-9-one and its polymeric precursor

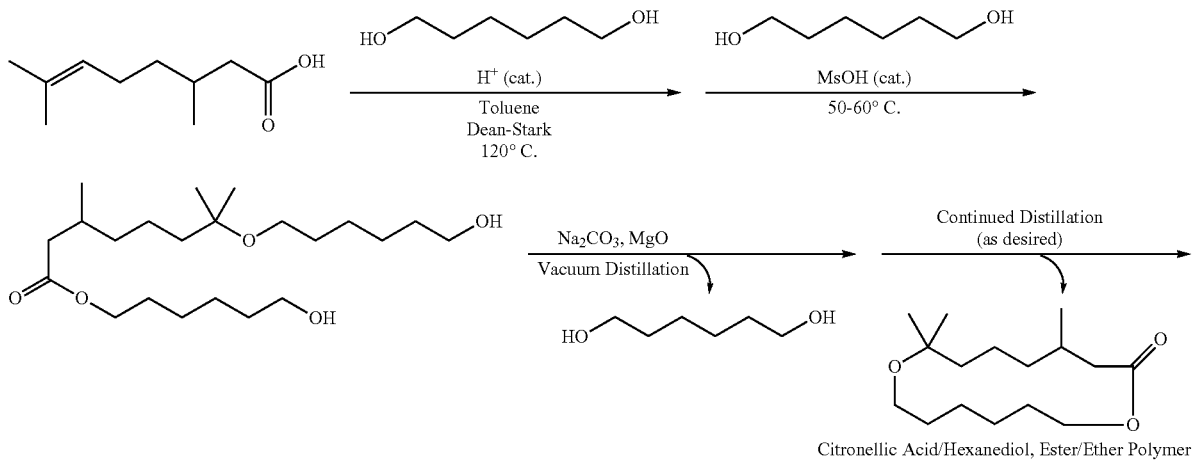

A mixture of citronellic acid (50 g, 0.29 mol), 1,6-hexanediol (69 g), methanesulfonic acid (5 g) and toluene (100 ml) in 500 mL was heated in a round bottom flask equipped with a Dean-Stark apparatus at 120° C. for 4 hours, removing the water formed in the Dean-Stark apparatus during the process. The reaction was cooled to 50-60° C. and additional 1,6-hexanediol (34.5 g) was added to the mixture. The reaction was then kept stirring at this temperature for 2 days before quenching the reaction with aqueous Na₂CO₃ (10% (w/v)) at room temperature (until pH=8). Ethyl acetate (100 ml) was added to the mixture and the phases were separated. The organic phase was washed with brine (150 ml) and then dried with Na₂SO₄. The Na₂SO₄ was filtered out and solvent was removed from the organic phase by evaporation, resulting in a red liquid residue (107 g). MgO (5 g) and Na₂CO₃ (5 g) were added to the residue and fractional distillation was performed by heating the mixture from 25 to 260° C. under vacuum. After removing most of the light fraction at 0.5-1.0 mbar, the final fraction containing the macrolactone product was distilled from the remaining reaction mixture at 200-270° C. under 0.3-0.5 mbar vacuum. Purification of the final distillation fraction by flash column chromatography gave 3.2 g of macrolactone product (silica gel, 2-7.5% ethyl acetate/heptane). Residue in the reaction vessel after distillation (20 g) comprised poly(11,15,15-trimethyl-1,8-dioxacyclopentadecan-9-one), MgO, and Na₂CO₃. NMR spectra for the macrolactone and polymer products are described below.

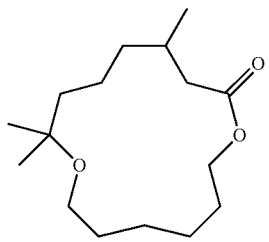 [SMILES: CC1CCCC(C)(C)OCCCCCCOC(=O)C1]

11,15,15-trimethyl-1,8-dioxacyclopentadecan-9-one

¹H NMR (CDCl₃, 500 MHz) δ 0.98 (d, J=7.5 Hz 3H, —CH₃), 1.12 (s, 3H, —CH₃), 1.13 (s, 3H, —CH₃), 1.23-1.71 (m, 16H, —CH₂—), 2.02-2.06 (m, 1H, —CH—), 2.12-2.17 (m, 1H, —CH₂—), 2.29-2.35 (m, 1H, —CH₂—), 3.27-3.30 (m, 2H, —CH₂O—), 4.05-4.09 (m, 1H, —CH₂O—), 4.13-4.17 (m, 1H, —CH₂O—).

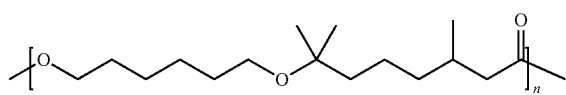

poly(11,15,15-trimethyl-1,8-dioxacyclopentadecan-9-one)

¹H NMR (CDCl₃, 400 MHz) δ 0.92 (d, J=6.4 Hz, 3H, —CH₃), 1.12 (s, 6H, —CH₃), 1.22-1.67 (m, 14H, —CH₂—), 1.93-1.93 (m, 1H, —CH—), 2.06-2.12 (m, 1H, —CH₂—), 2.26-2.31 (m, 1H, —CH₂—), 3.27 (t, J=6.8 Hz, 2H, —CH₂O—), 4.05 (m, J=6.8 Hz, 2H, —CH₂O—).

Example 3: Synthesis of 8,12,12-trimethyl-1,5-dioxacyclododecan-6-one and its polymeric precursor

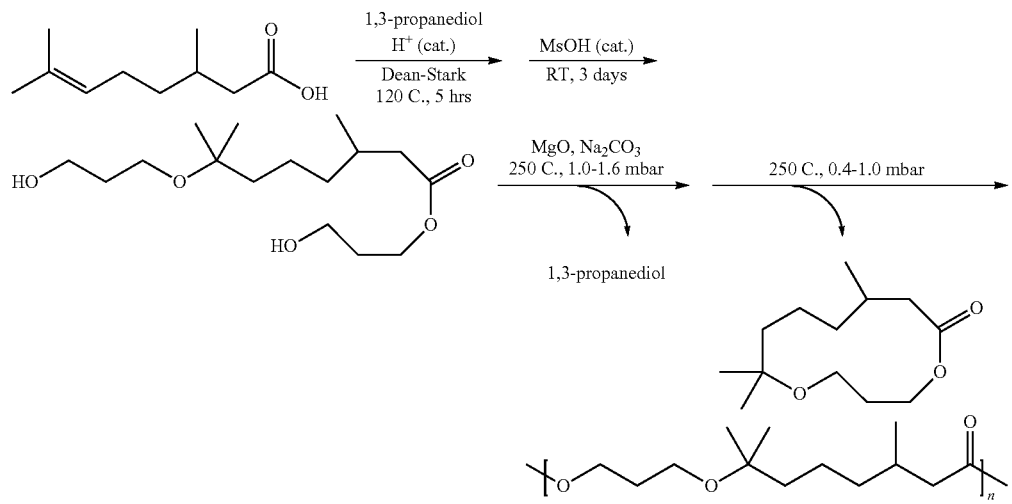

A mixture of citronellic acid (47.3 g, 0.278 mol), 1,3-propanediol (84.6 g, 1.112 mol), and methanesulfonic acid (4.73 g) was heated to 120° C. in a 500 mL round bottom flask equipped with distillation head for 5 hours, during which water was removed from the reaction via the distillation head. The reaction was then cooled to room temperature and left stirring for 3 days, at which time the reaction was quenched with aqueous NaCO₃ (10% (w/v)) at room temperature (until pH=8). Ethyl acetate (200 ml×2) was added to the reaction and the phases were separated. The organic phase (ethyl acetate solution) was washed with brine (150 ml), and dried with Na₂SO₄, which was subsequently removed by filtration. Solvent was then removed from the organic phase by evaporation, resulting in a red liquid residue (60 g). MgO (3 g) and NaCO₃ (3 g) were added to the residue and fractional distillation was performed by heating the mixture from 25 to 250° C. under 1.0-1.6 mbar vacuum. After removing a majority of light fraction at 1.0-1.6 mbar, the final fraction containing the macrolactone product was distilled from the remaining reaction mixture at 200-250° C. under 0.4-1.0 mbar vacuum. Purification of the final distillation fraction by flash column chromatography gave 0.84 g of macrolactone product (silica gel, 5-7.5% ethyl acetate/heptane). Residue in the reaction vessel after distillation (20 g) comprised poly(7-(3-hydroxypropoxy)-3,7-dimethyloctanoic acid) (FIG. 2), MgO, and Na₂CO₃. NMR spectra for the macrolactone and polymer products are described below.

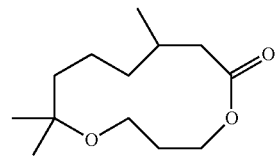

8,12,12-trimethyl-1,5-dioxacyclododecan-6-one

FIG. 1 depicts the ¹H NMR (400 MHz) spectrum of 8,12,12-trimethyl-1,5-dioxacyclododecan-6-one in CDCl₃. Chemical shift values (in ppm) for peaks in the spectrum are:

δ 0.96 (d, J=7.2 Hz, 3H, —CH₃), 1.09 (s, 3H, —CH₃), 1.11 (s, 3H, —CH₃), 1.14-1.40 (m, 5H, —CH₂—), 1.68-1.75 (m, 1H, —CH—), 1.85-1.97 (m, 3H, —CH₂—), 2.08-2.13 (m, 1H, —CH—), 2.41 (dd, J=12.8 Hz, J=2.4 Hz, 1H, —CH₂—), 3.34-3.39 (m, 1H, —CH₂O—), 3.45-3.50 (m, 1H, —CH₂O—), 4.07-4.13 (m, 1H, —CH₂O—), 4.20-4.25 (m, 1H, —CH₂O—).

poly(7-(3-hydroxypropoxy)-3,7-dimethyloctanoic acid), or alternatively, poly(8,12,12-trimethyl-1,5-dioxacyclododecan-6-one)

Figure 2:
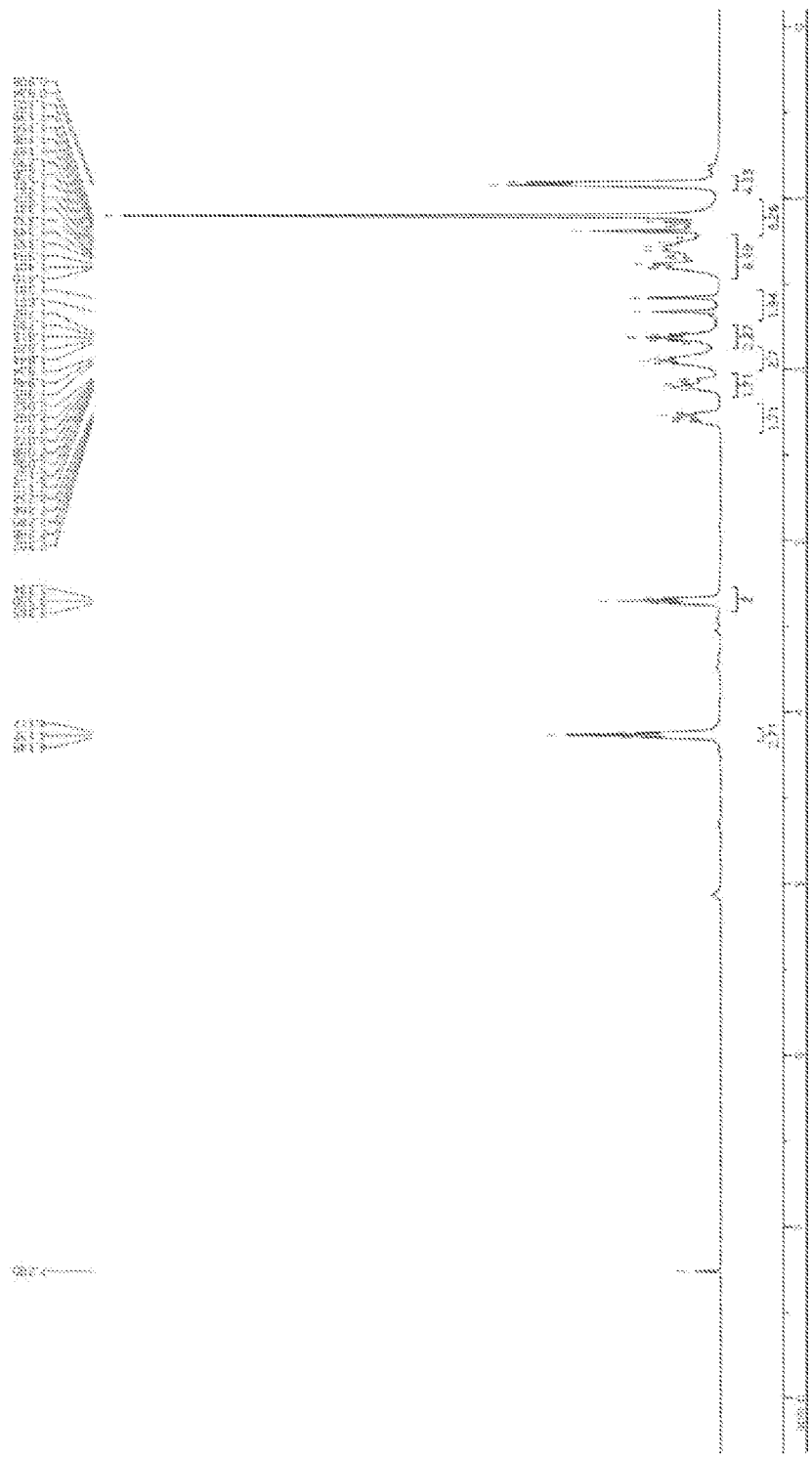
FIG. 2 is a $^1$H NMR spectrum of poly(7-(3-hydroxypropoxy)-3,7-dimethyloctanoic acid).

FIG. 2 depicts the ¹H NMR (400 MHz) spectrum of poly(7-(3-hydroxypropoxy)-3,7-dimethyloctanoic acid) in CDCl₃. Chemical shift values (in ppm) for peaks in the spectrum are: δ 0.92 (d, J=6.4 Hz, 3H, —CH₃), 1.10-1.41 (m, 11H, —CH₃, —CH₂—), 1.78-1.84 (m, 2H, —CH₂—), 1.93-1.97 (m, 2H, —CH—), 2.05-2.12 (m, 1H, —CH—), 2.25-2.35 (1, 2H, —CH—), 3.35 (t, 2H, J=6.4 Hz, —CH$_2$O—), 4.13 (t, 2H, J=6.4 Hz, —CH$_2$O—).

Example 4: Synthesis of 7,11,11-trimethyl-1,4-dioxacycloundecan-5-one and its polymeric precursor

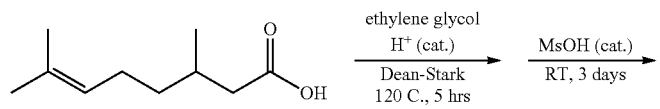

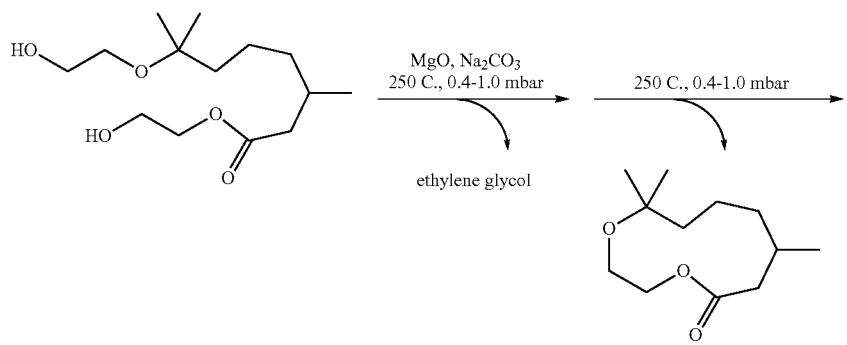

A mixture of citronellic acid (40 g, 0.235 mol), ethylene glycol (72.9 g, 1.175 mol), and methanesulfonic acid (2 g) was heated to 120° C. in a 500 mL round bottom flask equipped with distillation head for 5 hours, during which water was removed from the reaction via the distillation head. The reaction was then cooled to room temperature and left stirring for 3 days, at which time the reaction was quenched with aqueous NaCO$_3$ (10% (w/v)) at room temperature (until pH=8). Ethyl acetate (150 mL+50 mL) was added to the reaction and the phases were separated. The organic phase (ethyl acetate solution) was washed with brine (150 ml), and dried with Na$_2$SO$_4$, which was subsequently removed by filtration. Solvent was then removed from the organic phase by evaporation, resulting in a red liquid residue (60 g). MgO (3 g) and NaCO$_3$ (3 g) were added to the residue and fractional distillation was performed by heating the mixture from 25 to 250° C. under 0.4-1.0 mbar vacuum. After removing a majority of light fraction at 0.4-1.0 mbar, the final fraction containing the macrolactone product was distilled from the reaction at 250° C. under 0.4-1.0 mbar vacuum for 8 hours. Purification of the final distillation fraction by flash column chromatography gave 1.0 g of macrolactone product (silica gel, 5-7.5% ethyl acetate/heptane). Residue in the reaction vessel after distillation (15 g) comprised poly(7-(2-hydroxyethoxy)-3,7-dimethyloctanoic acid) (FIG. 4), MgO, and Na$_2$CO$_3$. NMR spectra for the macrolactone and polymer products are described below.

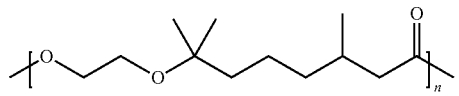

7,11,11-trimethyl-1,4-dioxacycloundecan-5-one

Figure 3:
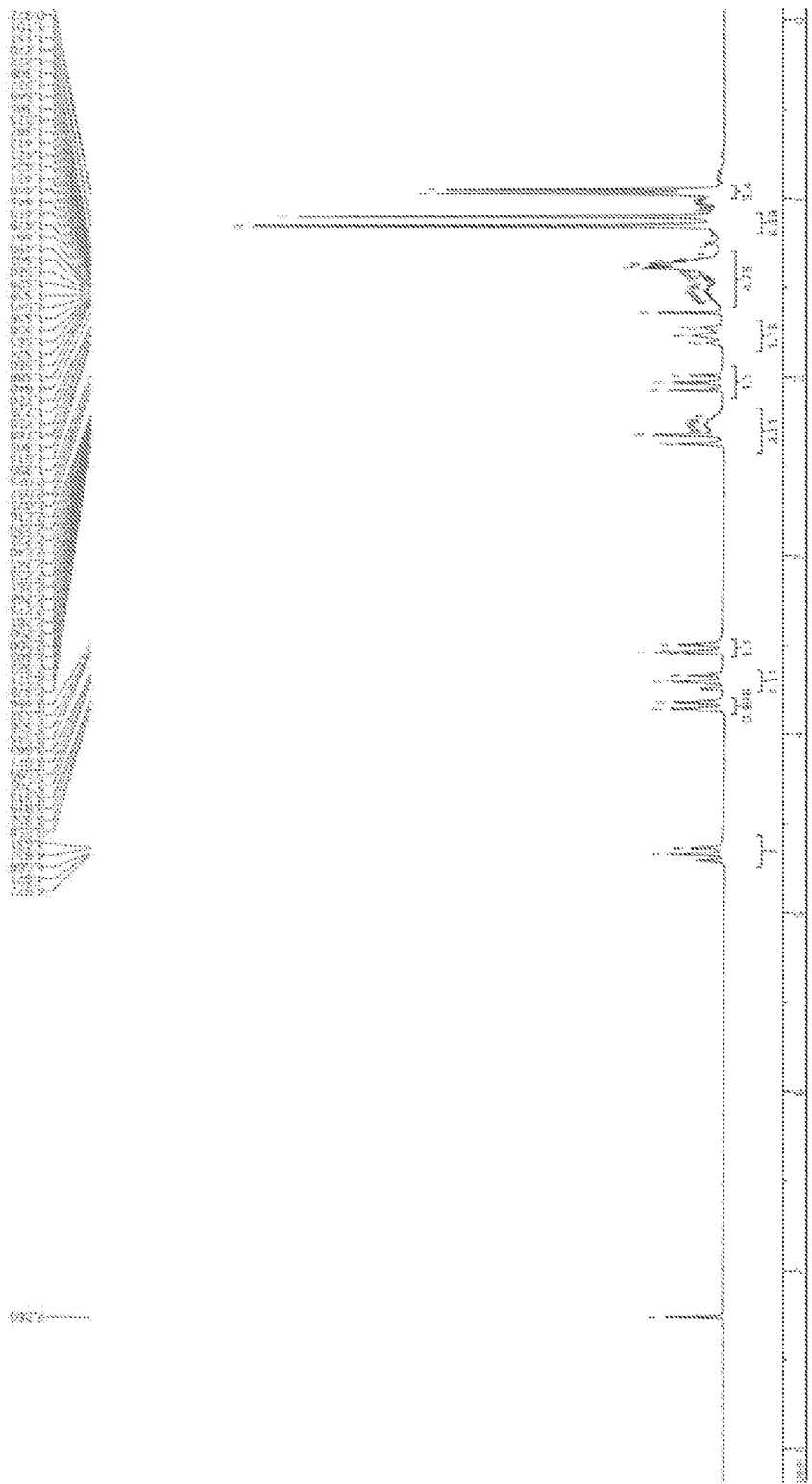
FIG. 3 is a $^1$H NMR spectrum of 7,11,11-trimethyl-1,4-dioxacycloundecan-5-one.

FIG. 3 depicts the $^1$H NMR (300 MHz) spectrum of 7,11,11-trimethyl-1,4-dioxacycloundecan-5-one in CDCl$_3$. Chemical shift values (in ppm) for peaks in the spectrum are: δ 0.96 (d, J=5.4 Hz, 3H, —CH$_3$), 1.10 (s, 3H, —CH$_3$), 1.15 (s, 3H, —CH$_3$), 1.27-1.64 (m, 5H, —CH$_2$—), 1.72-1.82 (m, 1H, —CH—), 1.99-2.07 (m, 1H, —CH$_2$—), 2.22-2.38 (m, 2H, —CH—), 3.52 (dt, J=12.6 Hz, J=1.8 Hz, 1H, —CH$_2$O—), 3.67-3.75 (m, 1H, —CH$_2$O—), 3.84 (td, J=11.7 Hz, J=1.8 Hz, 1H, —CH$_2$O—), 4.63-4.71 (m, 1H, —CH$_2$O—).

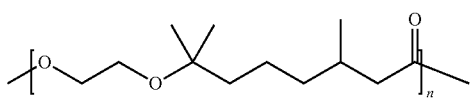

poly(7-(2-hydroxyethoxy)-3,7-dimethyloctanoic acid), or alternatively, poly(7,11,11-trimethyl-1,4-dioxacycloundecan-5-one)

Figure 4:
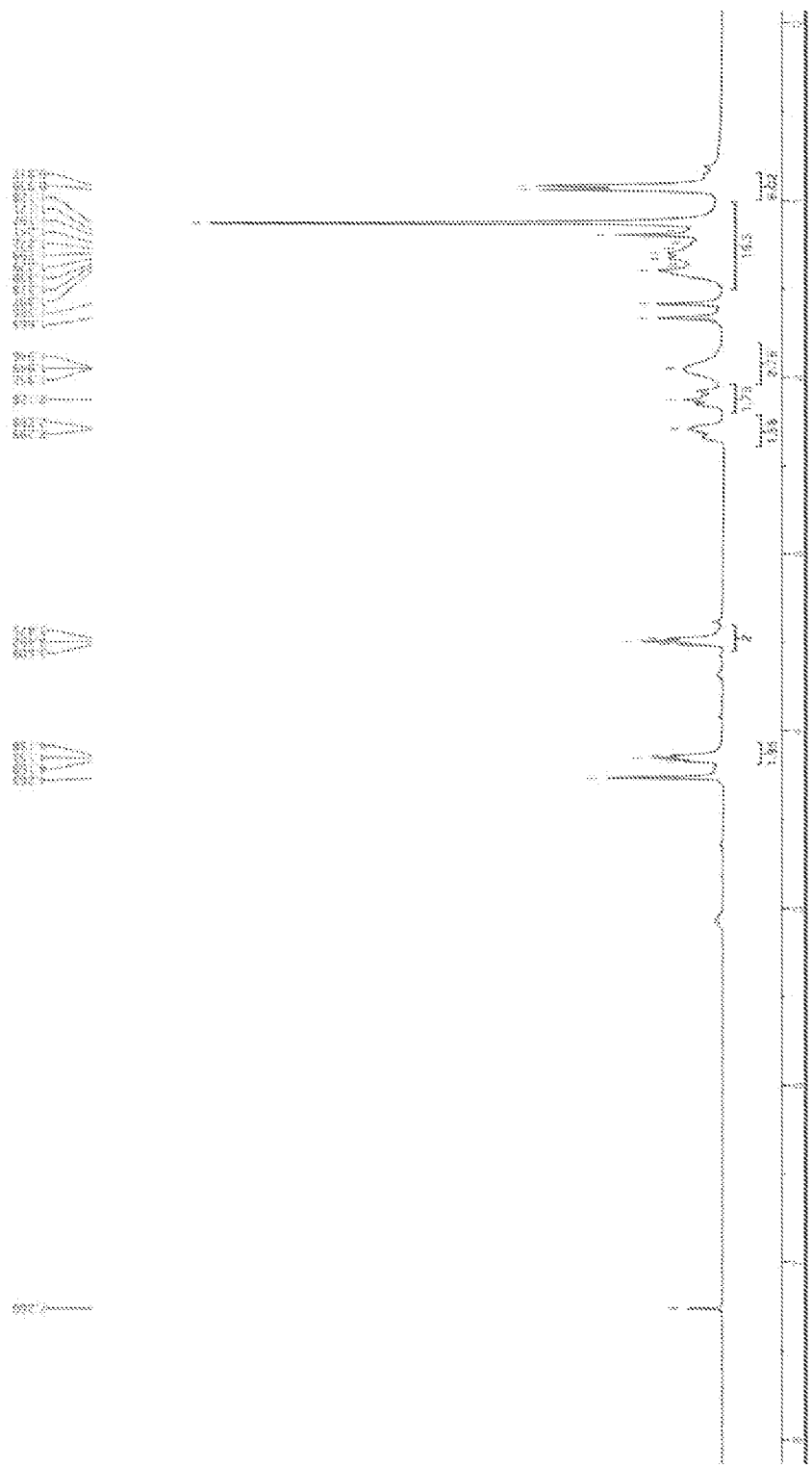
FIG. 4 is a $^1$H NMR spectrum of poly(7-(2-hydroxyethoxy)-3,7-dimethyloctanoic acid).

FIG. 4 depicts the $^1$H NMR (300 MHz) spectrum of poly(7-(2-hydroxyethoxy)-3,7-dimethyloctanoic acid) in CDCl$_3$. Chemical shift values (in ppm) for peaks in the spectrum are: δ 0.92 (d, J=6.6 Hz, 3H, —CH$_3$), 1.13-1.40 (m, 11H, —CH$_3$, —CH$_2$—), 1.86-1.95 (m, 2H, —CH$_2$—), 2.08-2.15 (m, 1H, —CH—), 2.28-2.36 (1, 1H, —CH—), 3.49 (t, 2H, J=5.1 Hz, —CH$_2$O—), 4.15 (t, 2H, J=5.1 Hz, —CH$_2$O—).

INCORPORATION BY REFERENCE

The entire disclosure of each of the patent documents and scientific articles referred to herein is incorporated by reference for all purposes.

EQUIVALENTS

The application can be embodied in other specific forms without departing from the spirit or essential characteristics thereof. The foregoing embodiments are therefore to be considered in all respects illustrative rather than limiting on the application described herein. Scope of the application is thus indicated by the appended claims rather than by the foregoing description, and all changes that come within the meaning and range of equivalency of the claims are intended to be embraced therein.

What is claimed:

1. A compound according to Formula I or Formula II:

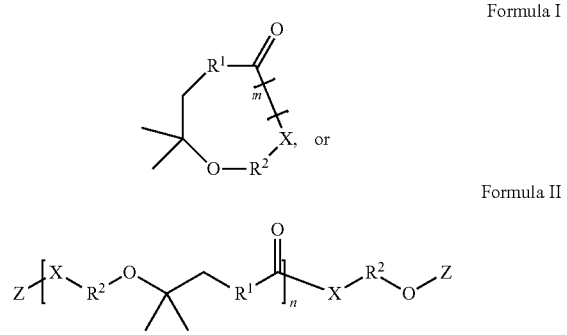

or a salt thereof, wherein,

R$^1$ is a bond, optionally substituted C$_1$-C$_{12}$ alkyl, optionally substituted C$_2$-C$_{12}$ alkenyl, or optionally substituted C$_2$-C$_{12}$ alkynyl;

R$^2$ is optionally substituted C$_1$-C$_{12}$ alkyl, optionally substituted C$_2$-C$_{12}$ alkenyl, or optionally substituted C$_2$-C$_{12}$ alkynyl;

X is O or NR$^x$;

R$^x$ is hydrogen or optionally substituted C$_1$-C$_{12}$ alkyl;

Z is hydrogen or

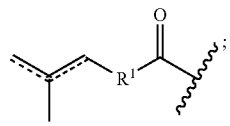

one of the ==== is a double bond and the other ==== is a single bond;

m is an integer between 1 and 10; and n is an integer between 1 and 100,000.

2. The compound of claim 1, wherein, for the compound of Formula I, the number of atoms comprising the ring structure is between 13 and 19.

3. The compound of claim 1, wherein X is O.

4. The compound of claim 1, wherein X is NH.

5. The compound of claim 1, wherein Z is hydrogen.

6. The compound of claim 1, wherein Z is

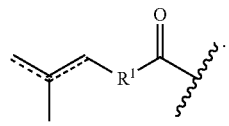

7. The compound of claim 1, wherein R$^1$ is optionally substituted linear C$_1$-C$_{12}$ alkyl branched C$_3$-C$_{12}$ alkyl, unsubstituted linear C$_1$-C$_{12}$ alkyl, optionally substituted linear C$_2$-C$_{12}$ alkenyl, unsubstituted linear C$_2$-C$_{12}$ alkenyl or branched C$_3$-C$_{12}$ alkenyl.

8. The compound of claim 1, wherein R$^2$ is optionally substituted linear C$_1$-C$_{12}$ alkyl, unsubstituted linear C$_1$-C$_{12}$ alkyl or branched C$_3$-C$_{12}$ alkyl.

9. The compound of claim 1, wherein R$^2$ is linear C$_1$-C$_{12}$ alkyl or branched C$_3$-C$_{12}$ alkyl substituted with one or more hydroxyl groups.

10. The compound of claim 1, wherein R$^2$ is optionally substituted linear C$_2$-C$_{12}$ alkenyl, unsubstituted linear C$_2$-C$_{12}$ alkenyl or branched C$_3$-C$_{12}$ alkenyl.

11. The compound of claim 1, wherein R$^2$ is optionally substituted linear C$_2$-C$_{12}$ alkynyl, unsubstituted linear C$_2$-C$_{12}$ alkynyl or branched C$_4$-C$_{12}$ alkynyl.

12. The compound of claim 1 according to Formula II, selected from:

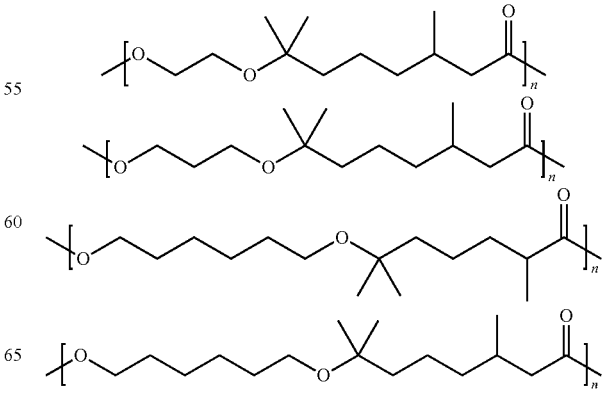

-continued
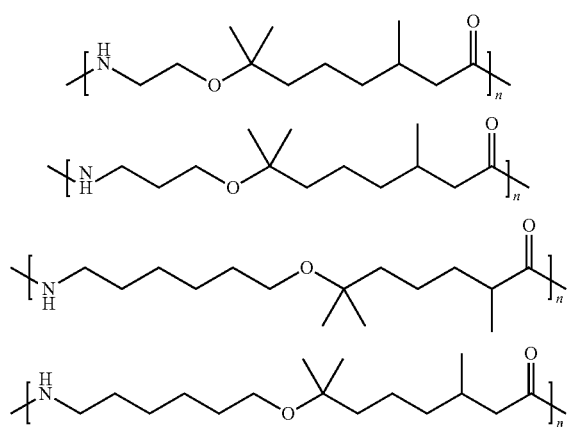
and salts thereof.
13. The compound of claim 1 according to Formula I, selected from:
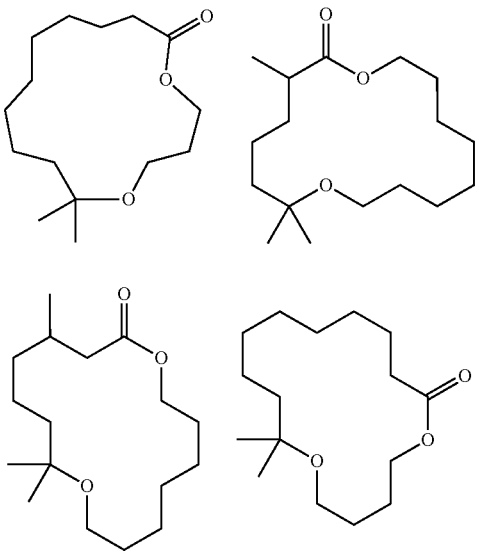
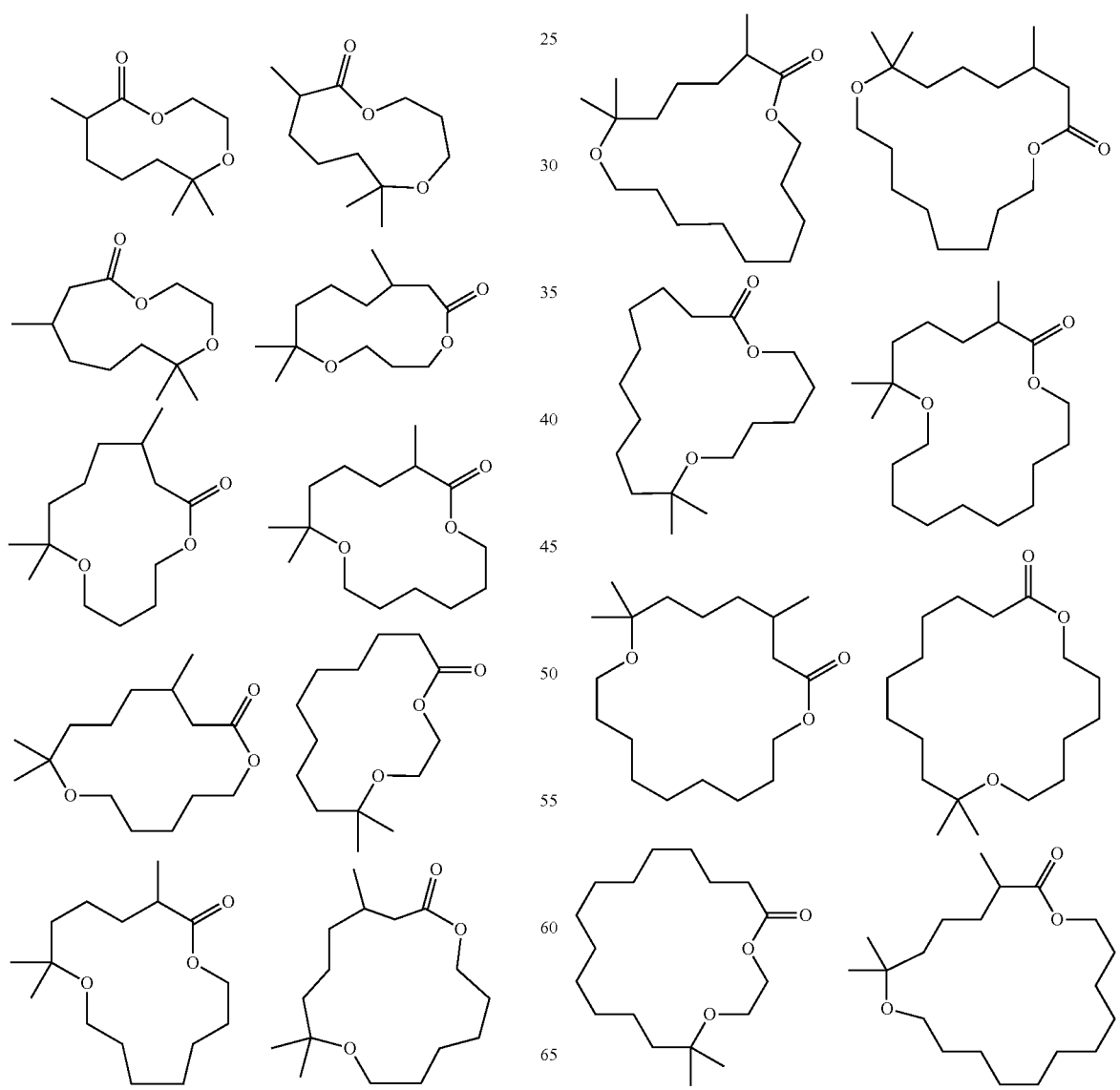

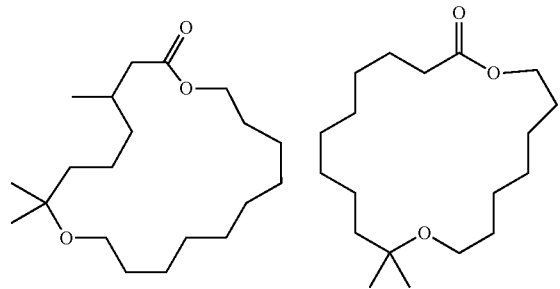
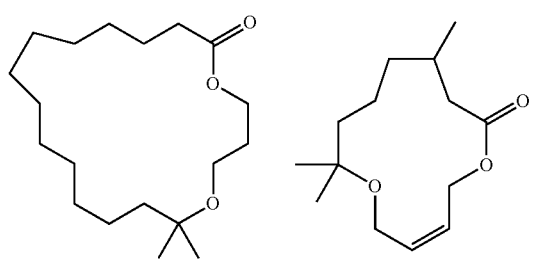
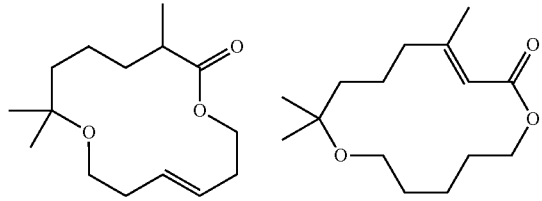
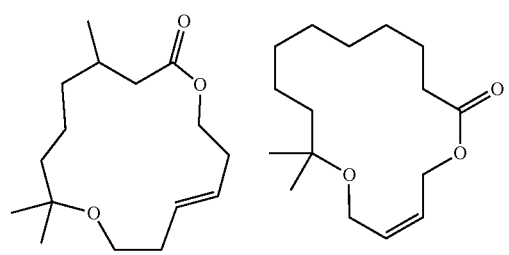
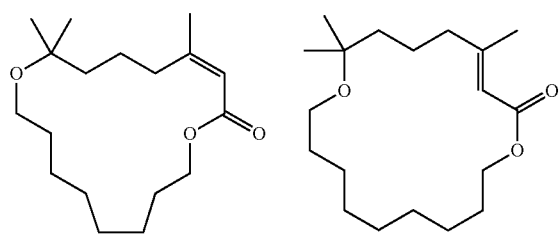
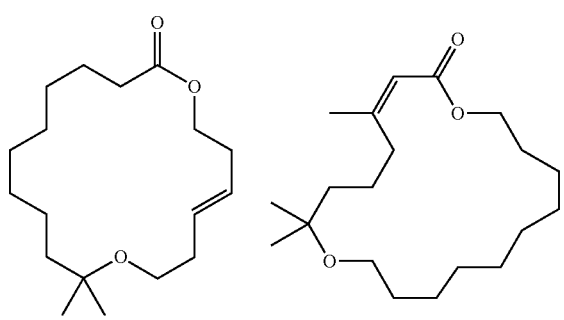
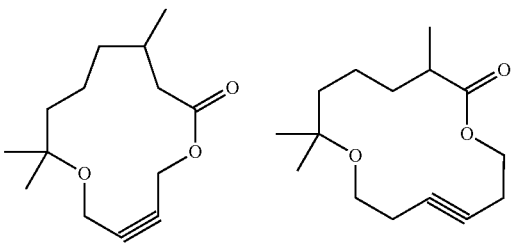
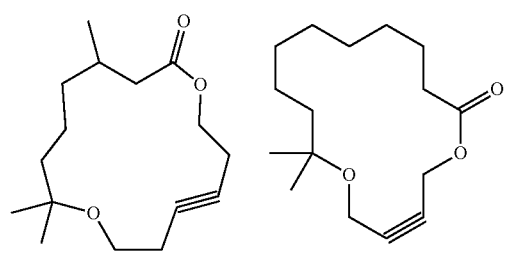
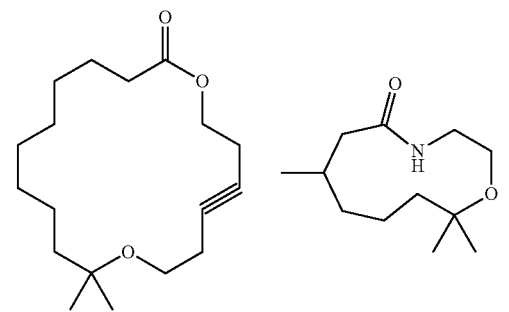
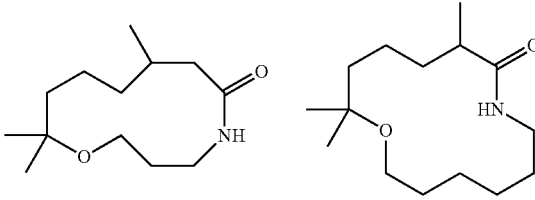
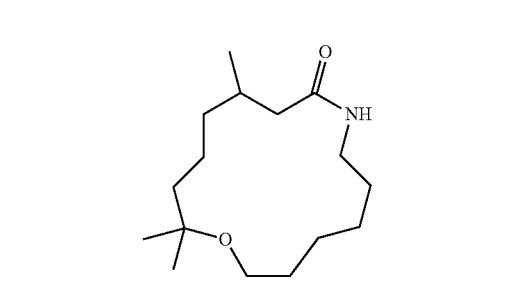
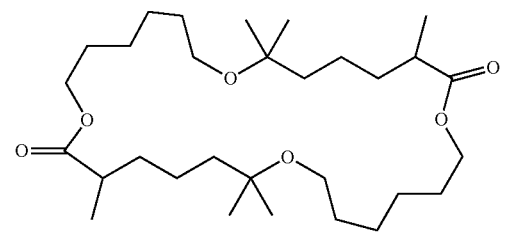

-continued

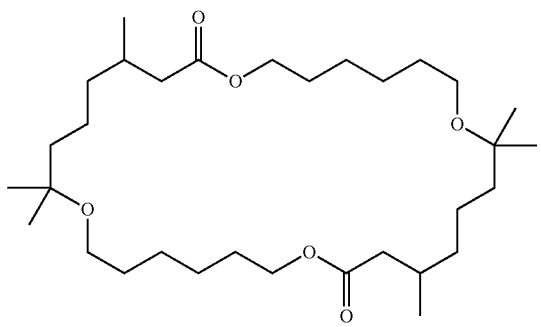

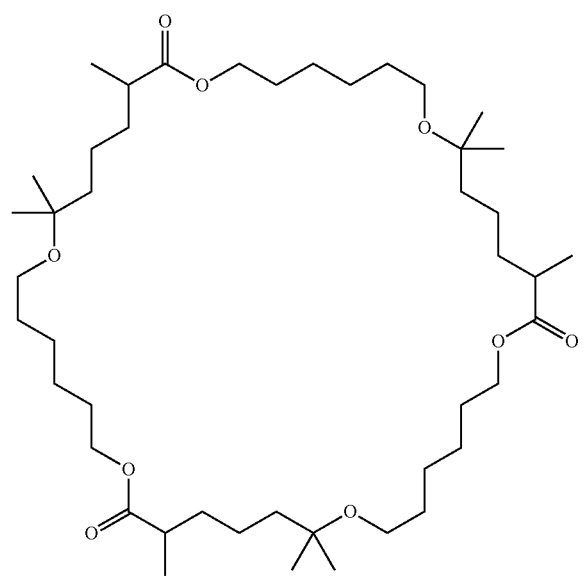

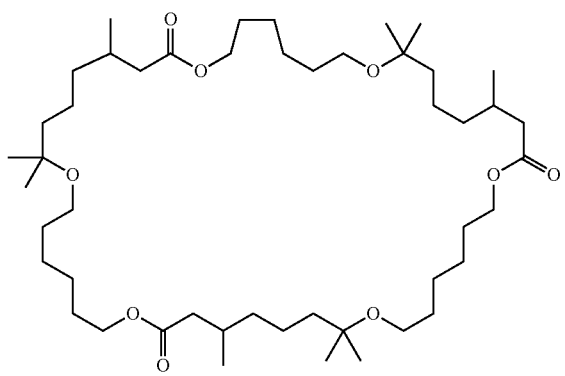

and salts thereof.

14. A method of producing a compound of claim 1, or a salt thereof, comprising reacting a compound of Formula III or Formula IV:

Formula III

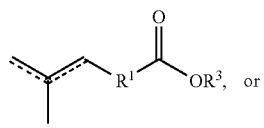

or

Formula IV

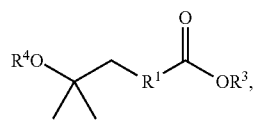

with a compound of Formula V:

Formula V

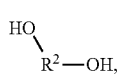

to obtain a reaction mixture comprising a compound of Formula I or Formula II, a salt thereof, or a combination thereof:

Formula I

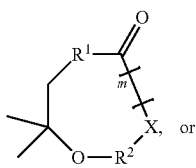

or

Formula II

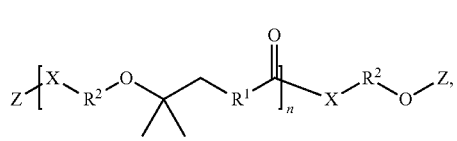

wherein,
$R^1$ is a bond, optionally substituted $C_1$-$C_{12}$ alkyl, optionally substituted $C_2$-$C_{12}$ alkenyl, or optionally substituted $C_2$-$C_{12}$ alkynyl;
$R^2$ is optionally substituted $C_1$-$C_{12}$ alkyl, optionally substituted $C_2$-$C_{12}$ alkenyl, or optionally substituted $C_2$-$C_{12}$ alkynyl;
$R^3$ is hydrogen, optionally substituted $C_1$-$C_{12}$ alkyl, optionally substituted $C_2$-$C_{12}$ alkenyl, or optionally substituted $C_2$-$C_{12}$ alkynyl;
$R^4$ is hydrogen, optionally substituted $C_1$-$C_{12}$ alkyl, optionally substituted $C_2$-$C_{12}$ alkenyl, or optionally substituted $C_2$-$C_{12}$ alkynyl;
X is O or $NR^x$;
$R^x$ is hydrogen or optionally substituted $C_1$-$C_{12}$ alkyl;
Z is hydrogen or

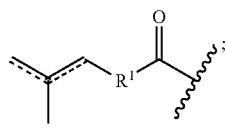

one of the ==== is a double bond and the other ==== is a single bond;
m is an integer between 1 and 10; and
n is an integer between 1 and 100,000;
wherein the ratio of the compound of Formula III or Formula IV to the compound of Formula V is 2 to 1 or greater; and
wherein the reaction of the compound of Formula III or Formula IV with the compound of Formula V comprises an esterification step, an etherification step, a first distillation step, and a second distillation step.

15. The method of claim 14, further comprising an amidation step, wherein a compound of Formula I, wherein X is O, reacts with $NH_3$ under an elevated pressure to obtain a corresponding compound of Formula I, wherein X is NH.

16. The method of claim 14, wherein the esterification step is performed at a first temperature that is greater than room temperature, and the etherification step is performed at a second temperature that is lower than the first temperature.

17. The method of claim 14, wherein the etherification step is quenched with a base.

18. The method of claim 14, wherein each of the first and second distillation steps is independently performed at a temperature that is between 25° C. and 260° C. and at a pressure between 0.1 and 1.6 mbar.

19. The method of claim 14, wherein $R^3$ is hydrogen.

20. The method of claim 14, wherein the compound of Formula III is selected from:

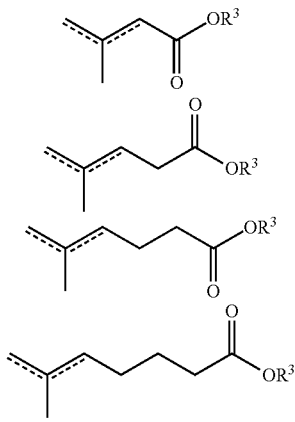

-continued

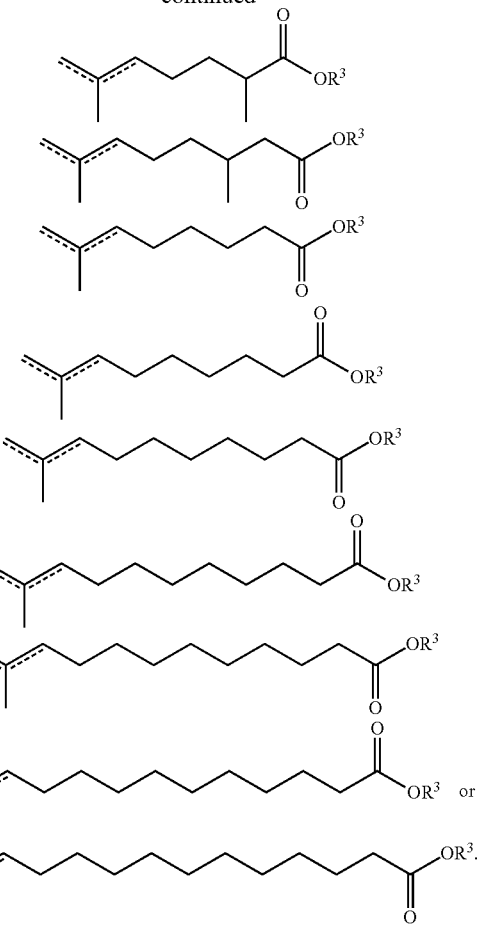

* * * * *